US011707555B2

(12) United States Patent
Wiley et al.

(10) Patent No.: US 11,707,555 B2
(45) Date of Patent: Jul. 25, 2023

(54) NANOFIBER REINFORCEMENT OF ATTACHED HYDROGELS

(71) Applicant: Duke University, Durham, NC (US)

(72) Inventors: Benjamin J. Wiley, Durham, NC (US); Huayu Tong, Durham, NC (US); Jiacheng Zhao, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 17/365,076

(22) Filed: Jul. 1, 2021

(65) Prior Publication Data

US 2022/0001079 A1  Jan. 6, 2022

Related U.S. Application Data

(60) Provisional application No. 63/183,670, filed on May 4, 2021, provisional application No. 63/046,944, filed on Jul. 1, 2020.

(51) Int. Cl.
| | |
|---|---|
| *A61L 27/52* | (2006.01) |
| *A61L 27/20* | (2006.01) |
| *A61L 24/02* | (2006.01) |
| *A61L 27/34* | (2006.01) |
| *A61L 27/32* | (2006.01) |

(Continued)

(52) U.S. Cl.
CPC ............... *A61L 27/52* (2013.01); *A61L 24/02* (2013.01); *A61L 27/20* (2013.01); *A61L 27/306* (2013.01); *A61L 27/32* (2013.01); *A61L 27/34* (2013.01); *A61L 27/3608* (2013.01); *A61L 2400/12* (2013.01); *A61L 2430/02* (2013.01); *A61L 2430/06* (2013.01)

(58) Field of Classification Search
None
See application file for complete search history.

(56) References Cited

U.S. PATENT DOCUMENTS

| 5,632,745 A | 5/1997 | Schwartz |
|---|---|---|
| 6,371,958 B1 | 4/2002 | Overaker |

(Continued)

FOREIGN PATENT DOCUMENTS

| CN | 1279997 C | 10/2006 |
|---|---|---|
| CN | 104208759 A | 12/2014 |

(Continued)

OTHER PUBLICATIONS

Yang et al. "A Synthetic Hydrogel Composite with the Mechanical Behavior and Durability of Cartilage", Adv. Funct. Mater., Jun. 2020, 20, 2003451, pp. 1-8. (Year: 2020).*

(Continued)

*Primary Examiner* — Carlos A Azpuru
*Assistant Examiner* — Casey S Hagopian
(74) *Attorney, Agent, or Firm* — Shay Glenn LLP

(57) ABSTRACT

Described herein are hydrogels attached to a base with the strength and fatigue comparable to that of cartilage on bone and methods of forming them. The methods and apparatuses described herein may achieve an attachment strength between a hydrogel and a substrate equivalent to the osteochondral junction. In some examples the hydrogel may be a triple-network hydrogel (such as BC-PVA-PAMPS) that is attached to a porous substrate (e.g., a titanium base) with the shear strength and fatigue strength equivalent to that of the osteochondral junction.

28 Claims, 15 Drawing Sheets

(51) Int. Cl.
*A61L 27/36* (2006.01)
*A61L 27/30* (2006.01)

(56) References Cited

U.S. PATENT DOCUMENTS

| | | | |
|---|---|---|---|
| 8,025,696 | B2 | 9/2011 | Osada et al. |
| 8,431,226 | B2 * | 4/2013 | Huerta ................ A61F 2/30767 |
| | | | 428/464 |
| 8,679,190 | B2 | 3/2014 | Myung et al. |
| 2001/0010023 | A1 | 7/2001 | Schwartz et al. |
| 2004/0101518 | A1 | 5/2004 | Vacanti et al. |
| 2005/0287187 | A1 | 12/2005 | Mansmann |
| 2008/0241214 | A1 | 10/2008 | Myung et al. |
| 2011/0054622 | A1 | 3/2011 | Muratoglu et al. |
| 2012/0265300 | A1 | 10/2012 | Mauck et al. |
| 2013/0274892 | A1 | 10/2013 | Lelkes et al. |
| 2014/0324169 | A1 | 10/2014 | Maher et al. |
| 2016/0287392 | A1 | 10/2016 | Patrick et al. |
| 2020/0390933 | A1 | 12/2020 | Williams et al. |
| 2021/0369915 | A1 | 12/2021 | Wiley et al. |
| 2022/0354995 | A1 | 11/2022 | Wiley et al. |

FOREIGN PATENT DOCUMENTS

| | | |
|---|---|---|
| CN | 104466140 A | 3/2015 |
| CN | 108601644 A | 9/2018 |
| CN | 208758338 U | 4/2019 |
| CN | 109789020 A | 5/2019 |
| CN | 110172126 B | 9/2020 |
| DE | 102009024133 A1 | 12/2010 |
| JP | H06-339490 A | 12/1994 |
| JP | 2010524567 A | 7/2010 |
| JP | 2014506177 A | 3/2014 |
| WO | WO2006/013612 A1 | 2/2006 |
| WO | WO2009/036431 A1 | 3/2009 |
| WO | 2018204315 A1 | 11/2018 |
| WO | 2019094426 A1 | 5/2019 |
| WO | WO-2019094426 A1 * | 5/2019 ......... A61F 2/30756 |
| WO | 2021067145 A1 | 4/2021 |
| WO | WO2022/235741 A1 | 11/2022 |

OTHER PUBLICATIONS

Yang, et al. A Synthetic Hydrogel Composite with the Mechanical Behavior and Durabilityy of Cartilage, Advanced Functional Materials, vol. 30 (Jun. 26, 2020) (8 pages) [retrieved on Sep. 20, 2021]. Retrieved from the Internet: <URL: https://onlinelibrary.wiley.com/doi/abs/10.1002/adfm.202003451>.

Zhao, et al. High-Strength Hydrogel Attachment through Nanofibrous Reinforcement, Advanced Healthcare Materials, vol. 10, Iss. 4 (Sep. 16, 2020) (Abstract, 1 page) [retrieved on Sep. 24, 2021]. Retrieved from the Internet: <URL: https://onlinelibrary.wiley.com/doi/10.1002/adhm.202001119>.

International Search Report and Written Opinion for PCT Application No. PCT/US2021/040031 dated Oct. 21, 2021.

Nakayama et al.; High mechanical strength double-network hydrogel with bacterial cellulose; Advanced Functional Materials; 14(11); pp. 1124-1128; Nov. 2004.

Wiley et al.; U.S. Appl. No. 17/845,881 entitled "Synthetic hydrogel composite ," filed Jun. 21, 2022.

Xinmeng; Construction of nanocellulose three-dimensional networks in polylactic acid and its influence on the foaming process; (Dissertion); retrived from the internet (https://wap.cnki.net/lunwen-1018132147.nh.html) 5 pages; on Jun. 16, 2022.

* cited by examiner

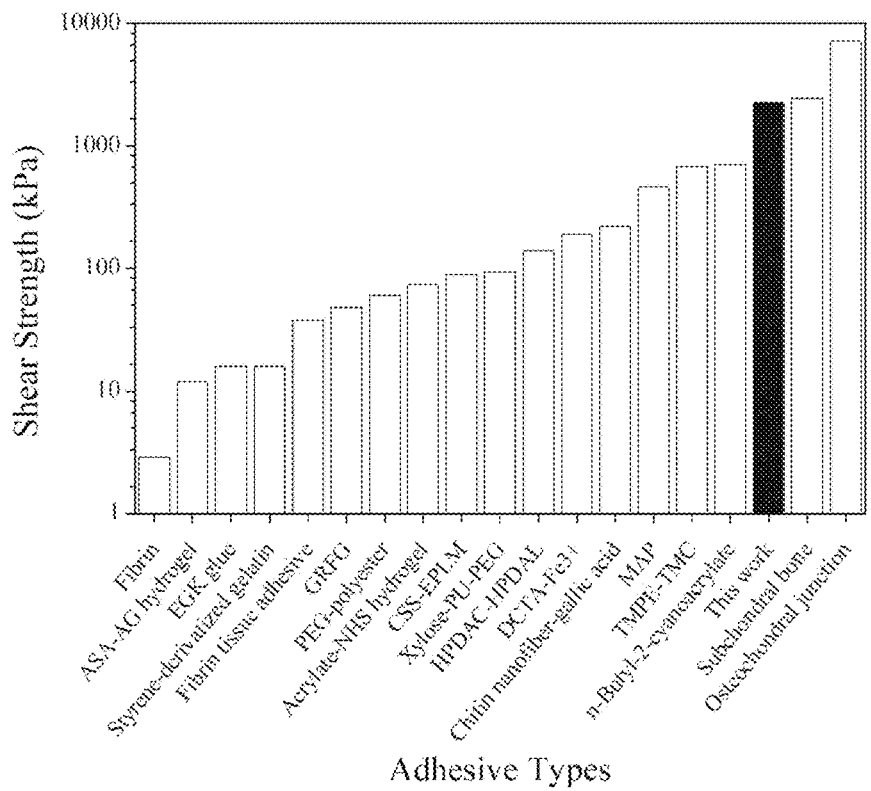

FIG. 9

| Adhesive Types | Adherend | Shear Strength (MPa) |
|---|---|---|
| a-TCP with stainless steel powder and phosphoserine | Porous titanium to BC-PVA-PAMPS hydrogel | 2.28 |
| Osteochondral junction | - | 7.25 |
| Subchondral bone | - | 2.45 |
| Fibrin | Sheep aortas | 0.0029 |
| Fibrin tissue adhesive | Human dura | 0.038 |
| GRFG | Bovine pericardial strips | 0.048 |
| n-Butyl-2-cyanoacrylate | Cartilage | 0.70 |
| Acrylate-NHS hydrogel | Collagen sheet | 0.074 |
| ASA-AG hydrogel | Porcine skin | 0.012 |
| Styrene-derivatized gelatin | Collagen film | 0.016 |
| EGK glue | Chicken skin | 0.016 |
| HPDAC-HPDAL | Porcine skin | 0.14 |
| CSS-EPLM | Porcine skin | 0.088 |
| Chitin nanofiber-gallic acid | Aluminum to hydrogel | 0.22 |
| TMPE-TMC | Chamois leather | 0.68 |
| Xylose-PU-PEG | Mussel | 0.094 |
| PEG-polyester | Porcine skin | ~0.04 |
| PEG-polyester | Bovine pericardium | 0.06 |
| MAP | Porcine intestine | 0.46 |
| DCTA-$Fe^{3+}$ | Articular cartilage | 0.19 |
| DCTA-$Fe^{3+}$ | Porcine skin | 0.025 |

FIG. 10A

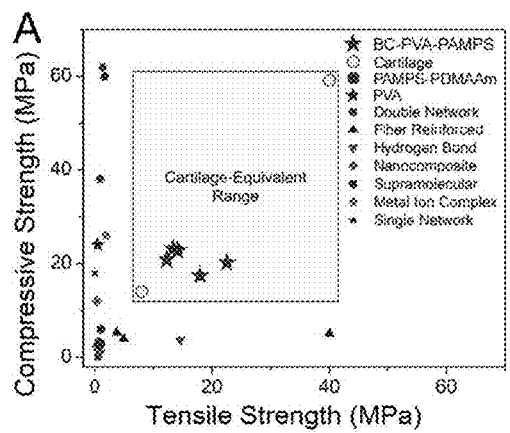
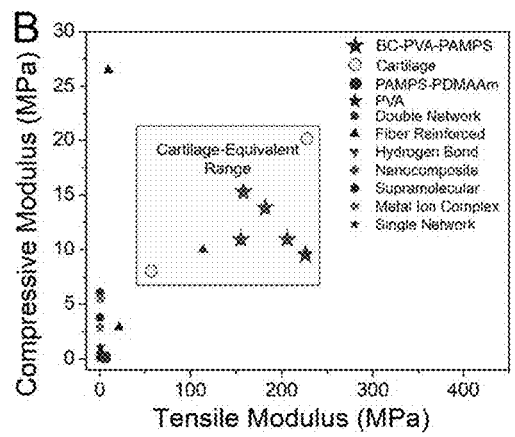
FIG. 10B  FIG. 10C
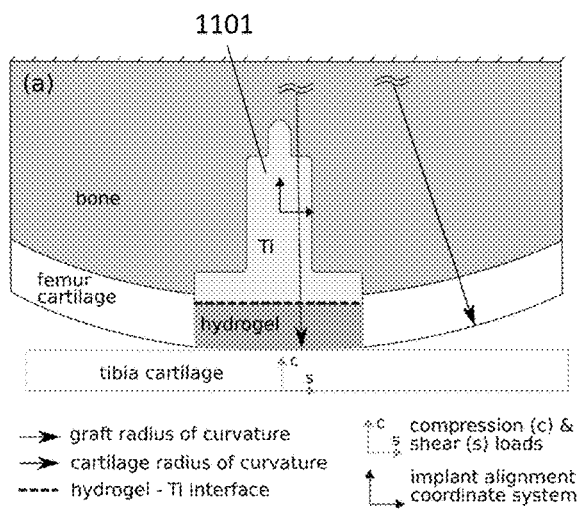
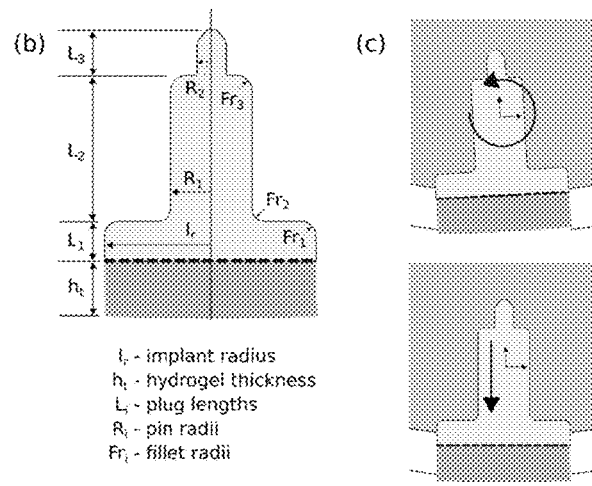
FIG. 11A  FIG. 11B  FIG. 11C

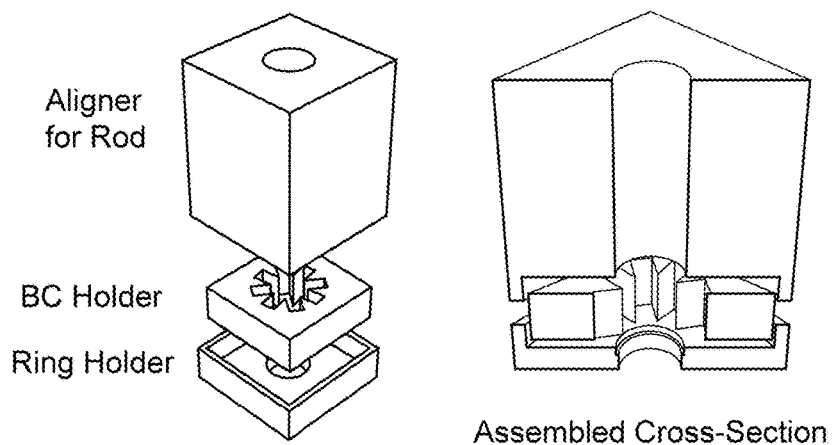
FIG. 18A      FIG. 18B
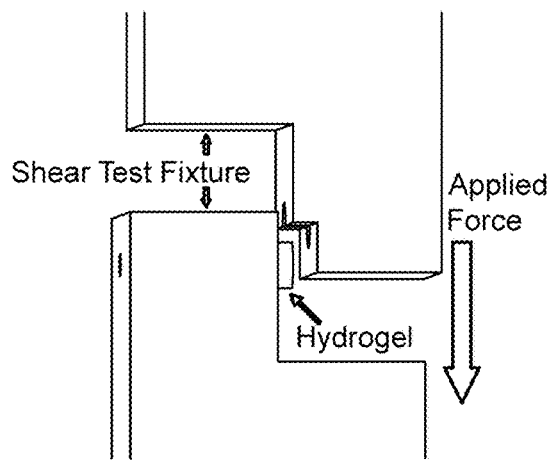
FIG. 19
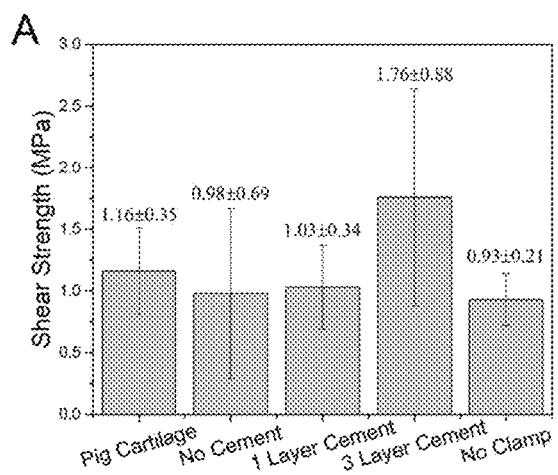 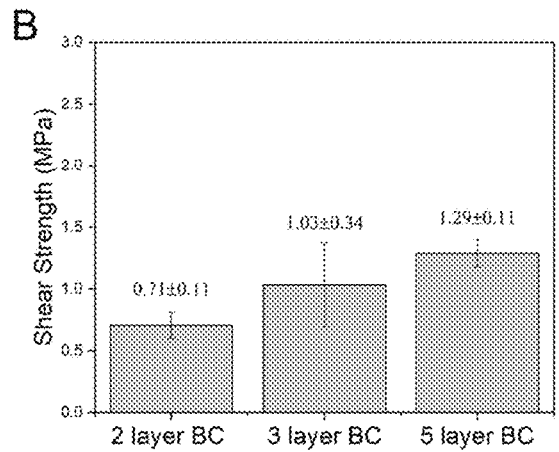
FIG. 20A      FIG. 20B

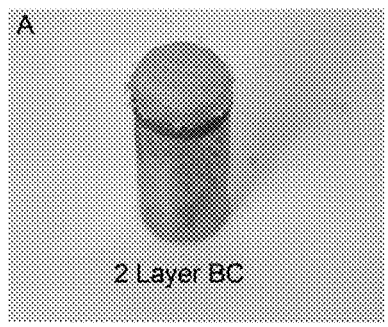 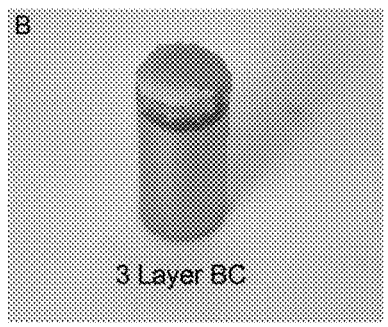 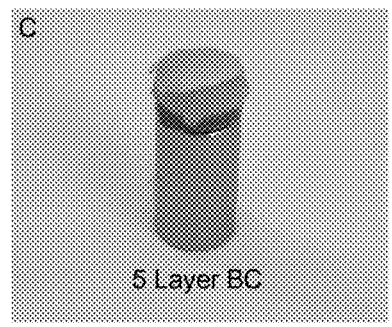
FIG. 22A    FIG. 22B    FIG. 22C
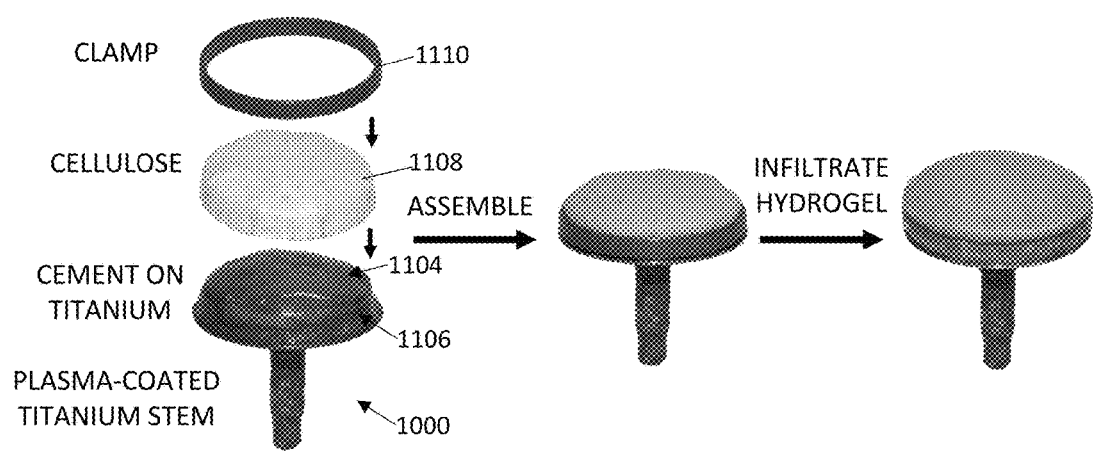
FIG. 23

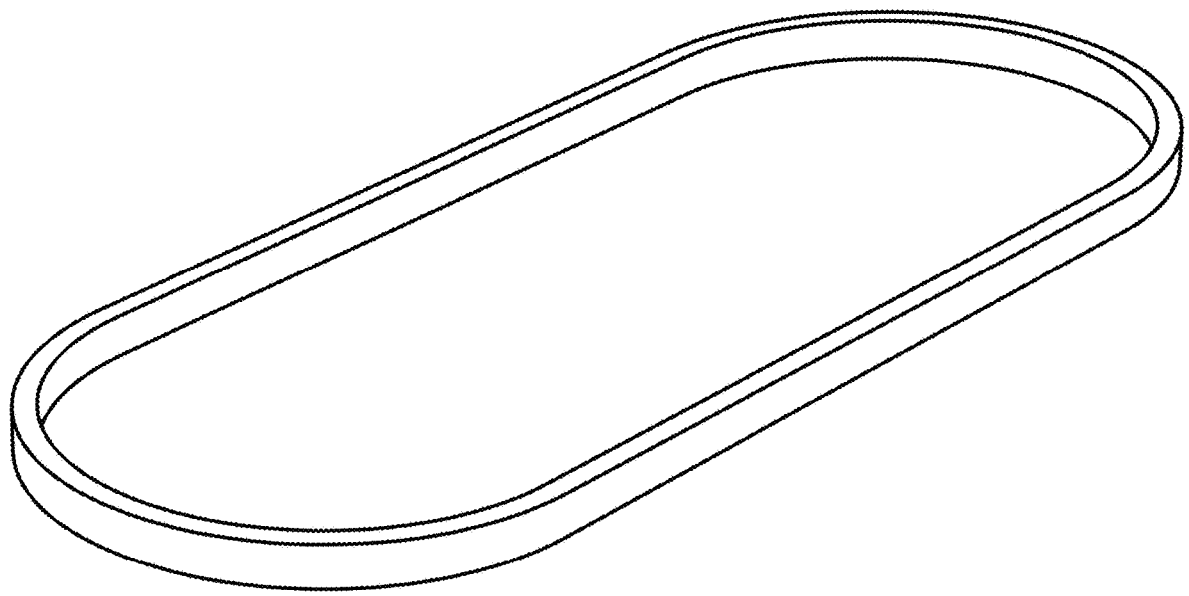

FIG. 24

```
┌─────────────────────────────────────────────┐
│ Cut one or more sheets of bacterial         │
│ cellulose (BC) to fit over engagement       │
│ surface and down sides of rim or lip region │
│ of implant.                                 │
│ 1301                                        │
└─────────────────────────────────────────────┘
                      │
                      ▼
┌─────────────────────────────────────────────┐
│ Secure the one or more sheets over the      │
│ engagement surface and down the sides of    │
│ rim or lip region (e.g., by clamp, and/or   │
│ adhesive cured under pressure) of implant.  │
│ 1303                                        │
└─────────────────────────────────────────────┘
                      │
                      ▼
┌─────────────────────────────────────────────┐
│ Infiltrate hydrogel component(s) into the   │
│ BC on the implant.                          │
│ 1305                                        │
└─────────────────────────────────────────────┘
```

FIG. 25

NANOFIBER REINFORCEMENT OF ATTACHED HYDROGELS

CROSS REFERENCE TO RELATED APPLICATIONS

This patent application claims priority to U.S. provisional patent application no. 63/046,944, titled "NANOFIBER REINFORCEMENT OF ATTACHED HYDROGELS," filed on Jul. 1, 2020, and U.S. provisional patent application No. 63/183,670, titled "HYDROGEL-COATED ORTHOPEDIC IMPLANTS," and filed on May 4, 2021, each of which are herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This disclosure relates generally to artificial cartilage materials in implants suitable for repair of cartilage, including specifically methods and compositions for attaching a polymer network hydrogel material to a surface of an implant, as well as implants including polymer network hydrogels.

BACKGROUND

Every year, approximately 900,000 people in the United States suffer from damage to the articular cartilage that lines the ends of the bones, with the knee being most commonly affected. Articular cartilage lesions have a limited intrinsic ability to heal and often lead to osteoarthritis. Although treatment of cartilage lesions can alleviate debilitating pain and delay the need for a total knee replacement, current strategies for cartilage restoration including bone marrow stimulation (microfracture), autologous cartilage cell implantation, and osteochondral transplantation typically have high failure rates (25-50% at 10 years), prolonged rehabilitation times (>12 months), can be very costly, and show decreasing efficacy in patients older than 40-50 years. Although alternatives such as focal joint resurfacing with traditional orthopedic materials (e.g. Cobalt-Chromium alloy, ultra-high-molecular-weight polyethylene) are being explored as an alternative strategy, these implants have limited ability to biologically integrate, and there are concerns they may contribute to joint degeneration through abnormal stress and wear on the opposing cartilage surface. It is widely acknowledged that a cost-effective procedure that can immediately restore the mechanical function of cartilage while enabling long-term biological integration is needed.

Hydrogels, polymer networks swollen with water, are a promising synthetic material for replacement of cartilage. However, there is currently no way to secure hydrogel into a cartilage defect site with the same shear strength as the junction between cartilage and bone. Thus, what is needed are methods and apparatuses that allow the use of a hydrogel having sufficiently cartilage-like properties to securely attach to an implant that may be used within the body.

Described herein are methods and apparatuses (e.g., implants) that may address these needs.

SUMMARY OF THE DISCLOSURE

Described herein are implants in which a hydrogel is bound to the surface of the implant with a strength that approximates that of healthy cartilage bound to bone, and methods of making and using these implants. These methods may secure a nanofibrous material (e.g., a nanofiber network) to a surface of an implant, such as a porous base, before infiltration of hydrogel components (e.g., a double hydrogel) into the nanofiber network. The nanofibrous material may be dry when attaching, or in some examples hydrated. The nanofibrous material may be secured using an adhesive or cement, and the adhesive or cement can penetrate into the porous nanofibrous network and create an interdigitating bond. In examples in which the porous nanofibrous network is dry, this interdigitating bond may be formed without the interference of water.

Although it would be beneficial for hydrogels to be attached to bone or to a porous substrate that integrates with bone with a shear strength similar to the shear strength of the osteochondral junction (e.g., 7.25 MPa), or at least the shear strength of subchondral bone (e.g., 2.45 MPa), current strategies for attaching hydrogels to a substrate result in shear strengths weaker than the bone-cartilage interface. Commonly used surgical adhesives include cyanoacrylate, gelating/resorcinol/formaldehyde (GRF), and fibrin. Cyanoacrylate can glue two pieces of cartilage together with a lap shear strength of 0.7 MPa. In addition to being too weak, cyanoacrylate can have cytotoxic effects due to the breakdown of cyanoacrylates into formaldehyde. GRF is weaker, exhibiting a shear strength of only 0.15 MPa with cartilage. Fibril glue is weaker still, with a shear strength of 0.036 MPa with skin. Many articles have been published on alternative adhesives for gluing a hydrogels or tissue (which is a hydrogel) to a substrate, but none of them exceed cyanoacrylate in shear strength.

One inherent problem with previous attachment strategies is that they seek adhesion to the hydrogel in the wet state, wherein water will inherently interfere in the attachment between the macromolecular component of the hydrogel and the substrate. A second problem with many of these strategies is that the adhesive cannot penetrate and interdigitate with the hydrogel, resulting in poor adhesion and concentration of stress at the hydrogel-substrate interface.

Described herein are implants and methods of making and using them that include a hydrogel for mimicking or replacing cartilage, that is interdigitated with a nanofibrous network, such as a cellulose nanofiber network. For example, an implant as described herein may include: an implant body including a first surface and a nanofiber network secured to the first surface (in some examples by a cement); and a hydrogel impregnated into the cross-linked cellulose nanofiber network to form a multiple-network hydrogel (such as a double-networks hydrogel or a triple-network hydrogel, etc.) extending from the first surface. The hydrogel is secured to the first surface with a shear strength that is greater than 1 MPa.

For example, described herein are implants comprising: an implant body including a first surface; and a nanofiber network bonded to the first surface by a cement; and a hydrogel impregnated into the nanofiber network to form a multiple-network hydrogel extending from the first surface, wherein the multiple-network hydrogel is secured to the first surface with a shear strength that is greater than 1 MPa.

An implant as described herein, having a hydrogel bonded to a first surface of the implant, may include: an implant body including the first surface, wherein the first surface is a porous titanium; a cross-linked cellulose nanofiber network, wherein the cross-linked cellulose nanofiber network is bonded to the first surface by a cement; and a hydrogel comprising polyvinyl alcohol (PVA) impregnated in the cross-linked cellulose nanofiber network to form a multiple-network hydrogel extending from the first surface, wherein the cement extends at least 5 microns into the cross-linked cellulose nanofiber network from the first surface but is not bonded to the hydrogel, further wherein the multiple-network hydrogel is secured to the first surface with a shear strength that is greater than 1 MPa In general, the multiple-network hydrogel may be a double-network hydrogel or a triple-network hydrogel. Any of these hydrogels may include polyvinyl alcohol (PVA). For example, the hydrogel impregnated into the nanofiber network may be a double network hydrogel that comprises polyvinyl alcohol (PVA), and poly(2-acrylamido-2-methyl-1-propanesulfonic acid sodium salt (PAMPS). In some examples the hydrogel impregnated into the nanofiber network may be a double network hydrogel comprising one or more of: poly-(N,N'-dimethyl acrylamide) (PDMAAm), copolymers of 1-vinylimidazole and methacrylic acid, amphiphilic triblock copolymers, polyampholyte hydrogels, a PVA-tannic acid hydrogel, a poly(N-acryloyl) glycinamide hydrogel, polyacrylic acid-acrylamide-C18 hydrogel, guanine-boric acid reinforced PDMAAm, polyelectrolyte hydrogels, a poly(acrylonitrile-co-1-vinylimidazole) hydrogel (e.g., a mineralized poly(acrylonitrile-co-1-vinylimidazole) hydrogel), a polyacrylic acid-Fe3+-chitosan hydrogel, a poly(methacrylic acid) gel, a graphene oxide/Xonotlite reinforced polyacrylamide (PAAm) gel, a poly(stearyl methacrylate)-polyacrylic acid gel, an annealed PVA-polyacrylic acid hydrogel, supramolecular hydrogels from multiurea linkage segmented copolymers, polyacrylonitrile-PAAm hydrogel, a microsilica reinforced DMA gel, an agar-polyhydroxyethylmethacrylate gel, a polyfacryloyloethyltrimethylammonium chloride hydrogel, a poly(3-(methylacryloylamino)propyl-trimethylammonium chloride hydrogel, a poly(sodium p-styrenbesulfonate) hydrogel, a polyethylene glycol diacrylate hydrogel, a polyethylene glycol hydrogel, or hydrogels composed of a combination of these polymers.

The implant may be configured as a medical implant, and may include a tissue engaging portion (e.g., a bone engaging portion such as a rod, screen, nail, etc.). The first surface of the implant may be porous. For example, the first surface may be greater than 40% porous to a depth of 1 mm or greater.

In any of these examples, the nanofiber network may comprise a cellulose nanofiber network. For example, the nanofiber network may comprise a cross-linked cellulose nanofiber network. In some examples the nanofiber network comprises at least one of: electrospun polymer nanofibers, poly(vinyl alcohol) (PVA) nanofibers, aramid nanofibers, aramid-PVA nanofibers, wet-spun silk protein nanofiber, chemically crosslinked cellulose nanofiber, or polycaprolactone (PCL) fibers.

The nanofiber network may be secured to the implant (e.g., to the first surface of the implant) by any appropriate method. For example, the nanofiber network may be secured to the first surface of the implant by a cement, such as an α-TCP cement. In some examples the cement comprises one or more of: zinc oxide eugenol, glass ionomer, calcium silicate, polycarboxylate cement, zinc phosphate, acrylate or methacrylate resin cements, and resin-modified glass ionomer cement. In general, the cement may extend at least 5 microns into the nanofiber network from the first surface. The cement may not be bonded to the hydrogel. The cement may comprise phosphoserine (PPS). In some examples, the cement comprises stainless steel powder (SSP). In any of the apparatuses described herein, at least a portion of the nanofiber network may be mineralized.

In general, the cement may be bonded to the nanofiber network but not be bonded to the hydrogel directly. This may be a consequence of the method of forming the multiple-network hydrogel, in which the nanofiber network (e.g., the cellulose nanofiber network) is first secured (e.g., cemented) to the implant body, before impregnating the hydrogel. The cement may be cured onto the nanofiber network so that it does not directly bond to the hydrogel.

The implant may be formed of any appropriate biocompatible material. For example, the surface of the implant body may be titanium. The surface of the implant body may be one or more of: a stainless steel alloy, a titanium alloy, a Co—Cr alloy, tantalum, gold, niobium, bone, Al oxide, Zr oxide, hydroxyapatite, tricalcium phosphate, calcium sodium phosphosilicate, poly(methyl methacrylate), polyether ether ketone, polyethylene, polyamide, polyurethane, or polytetrafluoroethylene.

For example, described herein are implant having a hydrogel bonded to a first surface of the implant, the implant comprising: an implant body including the first surface, wherein the first surface is porous; and a cross-linked cellulose nanofiber network, wherein the cross-linked cellulose nanofiber network is secured to the first surface; and a hydrogel comprising polyvinyl alcohol (PVA) impregnated in the cross-linked cellulose nanofiber network to form a multiple-network hydrogel extending from the first surface, wherein the multiple-network hydrogel is secured to the first surface with a shear strength that is greater than 1 MPa.

In some examples the implant having a hydrogel bonded to a first surface of the implant includes: an implant body including the first surface, wherein the first surface is porous; and a cross-linked cellulose nanofiber network, wherein the cross-linked cellulose nanofiber network is bonded to the first surface by a cement; and a hydrogel comprising polyvinyl alcohol (PVA) impregnated in the cross-linked cellulose nanofiber network to form a multiple-network hydrogel extending from the first surface, wherein the multiple-network hydrogel is secured to the first surface with a shear strength that is greater than 1 MPa.

An implant having a hydrogel bonded to a first surface of the implant may include: an implant body including the first surface, wherein the first surface is porous; and a cross-linked cellulose nanofiber network, wherein the cross-linked cellulose nanofiber network is bonded to the first surface by a cement; and a double-network of polyvinyl alcohol (PVA), and poly(2-acrylamido-2-methyl-1-propanesulfonic acid sodium salt (PAMPS) impregnated in the cross-linked cellulose nanofiber network to form a triple-network hydrogel extending from the first surface, wherein the triple-network hydrogel is secured to the first surface with a shear strength that is greater than 1 MPa.

As mentioned, the first surface may be porous. For example, the first surface may be 20% or greater (30% or greater, 40% or greater, 50% or greater, 60% or greater, 70% or greater, etc.) porous, to a depth of 0.5 mm or greater (e.g., 0.6 mm, 0.7 mm, 0.8 mm, 0.9 mm, 1 mm or greater, etc.). As used herein, the percentage that the surface if porous (e.g., the percent porosity of the surface) may refer to the percentage of the surface within the depth that is absent, forming open spaces within the surface. These open spaces may refer to pores, some of which may be connected (e.g., in fluid connection) with each other.

The nanofiber network may comprise a cross-linked nanofiber network. In some variations the nanofiber network comprises a cellulose nanofiber network (e.g., a bacterial cellulose, BC, network). The nanofiber network may comprise at least one of: electrospun polymer nanofibers, poly(vinyl alcohol) (PVA) nanofibers, aramid nanofibers, aramid-PVA nanofibers, wet-spun silk protein nanofiber, chemically crosslinked cellulose nanofiber, or polycaprolactone (PCL) fibers.

The cement may be any appropriate cement, such as (but not limited to) α-TCP cement. The cement may be one or more of: zinc oxide eugenol, glass ionomer, calcium silicate, polycarboxylate cement, zinc phosphate, resin-based (dental) cements, such as acrylate or methacrylate resin cements, which may contain silicate or other types of fillers in an organic resin matrix (for example, a methacrylate cement such as "RelyX™ Unicem 2 Self-Adhesive Resin Cement," or "RelyX™ Ultimate Adhesive Resin Cement"), and resin-modified glass ionomer cement. The cement may include an adhesive, such as (but not limited to) phosphoserine (PPS). In some variations the cement may include particles for reinforcement, such as stainless steel particles (e.g., stainless steel powder, SSP).

In any of these apparatuses (e.g., devices, systems, including implants), at least a portion of the nanofiber network may be mineralized. For example, at least a portion, such as the region near the interface with the surface, may be mineralized with hydroxyapatite. The mineralization may extend at least 5 microns into the nanofiber network (e.g., at least 7 microns, at least 8 microns, at least 9 microns, at least 10 microns, at least 15 microns, at least 20 microns, etc.) from the surface.

The double network hydrogel may include polyvinyl alcohol (PVA), and poly(2-acrylamido-2-methyl-1-propanesulfonic acid sodium salt (PAMPS). In some variations, the double network hydrogel comprises poly-(N,N'-dimethyl acrylamide) (PDMAAm), copolymers of 1-vinylimidazole and methacrylic acid, amphiphilic triblock copolymers, polyampholyte hydrogels, a PVA-tannic acid hydrogel, a poly(N-acryloyl) glycinamide hydrogel, polyacrylic acid-acrylamide-C18 hydrogel, guanine-boric acid reinforced PDMAAm, polyelectrolyte hydrogels, a poly(acrylonitrile-co-1-vinylimidazole) hydrogel (e.g., a mineralized poly(acrylonitrile-co-1-vinylimidazole) hydrogel), a polyacrylic acid-Fe3+-chitosan hydrogel, a poly(methacrylic acid) gel, a graphene oxide/Xonotlite reinforced polyacrylamide (PAAm) gel, a poly(stearyl methacrylate)-polyacrylic acid gel, an annealed PVA-polyacrylic acid hydrogel, supramolecular hydrogels from multiurea linkage segmented copolymers, polyacrylonitrile-PAAm hydrogel, a microsilica reinforced DMA gel, a agar-polyhydroxyethylmethacrylate gel, a polyfacryloyloethyltrimethylammonium chloride hydrogel, a poly(3-(methylacryloylamino)propyl-trimethyl-ammonium chloride hydrogel, a poly(sodium p-styrenesulfonate) hydrogel, a polyethylene glycol diacrylate hydrogel, a polyethylene glycol hydrogel, or hydrogels composed of a combination of these polymers.

In general, the cement is not bonded to the hydrogel; the cement is only bonded to the nanofiber network.

Any appropriate implant may be used. The surface of the implant, at least at the region to which the nanofiber network is cemented, may be titanium, stainless steel, etc. For example, the surface of the implant body may comprise one or more of: a stainless steel alloy, a titanium alloy, a Co—Cr alloy, tantalum, gold, niobium, bone, Al oxide, Zr oxide, hydroxyapatite, tricalcium phosphate, calcium sodium phosphosilicate, poly(methyl methacrylate), polyether ether ketone, polyethylene, polyamide, polyurethane, or polytetrafluoroethylene.

Also described herein are methods. For example, methods of attaching a hydrogel to a surface so that the hydrogel is secured to the surface with a shear strength of greater than 1 MPa. Any of these methods may include: securing a dry nanofiber network to the surface; and infiltrating the nanofiber network with a hydrogel to form a multiple-network hydrogel on the surface. As mentioned above, securing may comprise cementing. For example, cementing may include bonding the nanofiber network without bonding the double-network hydrogel. In some examples cementing comprises applying an α-TCP cement. Cementing may include applying a cement comprising one or more of: zinc oxide eugenol, glass ionomer, calcium silicate, polycarboxylate cement, zinc phosphate, and resin-modified glass ionomer cement. Cementing may comprise extending the cement at least 5 microns into the nanofiber network from the first surface. Cementing the dry nanofiber network to the surface may comprise cementing the dry nanofiber network to the surface, wherein the surface is greater than 40% porous to a depth of 1 mm or greater.

In general, the outer surface of the hydrogel may be formed to be smooth (e.g., to have a roughness of less than 30 microns). For example, the methods described herein may include mechanically polishing an outer surface of the hydrogel to a roughness of less than 30 microns. In some cases the outer surface may be formed smooth by molding, including molding the heated polymer using a smooth mold. For example, infiltrating the nanofiber network with hydrogel may include molding the hydrogel so that an outer surface of the hydrogel has a roughness of less than 30 microns. Molding the outer surface may also allow the manufacturer to form the outer surface into any desired shape. For example, the shape may be concave, convex, saddle shaped, etc. Any desired shape (and smoothness) may be formed, e.g. by molding and/or polishing.

In any of these methods securing the (e.g., dry) nanofiber network may include securing, such as cementing, a freeze-dried nanofiber network. As mentioned above, any of these devices and methods may use a dry nanofiber network that comprises a cellulose nanofiber network. The dry nanofiber network may comprise at least one of: electrospun polymer nanofibers, poly(vinyl alcohol) (PVA) nanofibers, aramid nanofibers, aramid-PVA nanofibers, wet-spun silk protein nanofiber, chemically crosslinked cellulose nanofiber, or polycaprolactone (PCL) fibers.

Any of the methods described herein may include rehydrating the nanofiber network. Including rehydrating it after it has been secured to the implant surface.

In general, infiltrating may comprise infiltrating the nanofiber network with any appropriate hydrogel, and in particular a PVA containing hydrogel. For example, infiltrating may comprise infiltrating the nanofiber network with a double-network hydrogel comprising polyvinyl alcohol (PVA), and poly(2-acrylamido-2-methyl-1-propanesulfonic acid sodium salt (PAMPS) to form a triple-network hydrogel on the porous surface.

In any of these methods and apparatuses, infiltrating may comprise infiltrating the nanofiber network with a double-network hydrogel comprising one or more of: poly-(N,N'-dimethyl acrylamide) (PDMAAm), copolymers of 1-vinylimidazole and methacrylic acid, amphiphilic triblock copolymers, polyampholyte hydrogels, a PVA-tannic acid hydrogel, a poly(N-acryloyl) glycinamide hydrogel, polyacrylic acid-acrylamide-C18 hydrogel, guanine-boric acid reinforced PDMAAm, polyelectrolyte hydrogels, a poly(acrylonitrile-co-1-vinylimidazole) hydrogel (e.g., a mineralized poly(acrylonitrile-co-1-vinylimidazole) hydrogel), a polyacrylic acid-Fe3+-chitosan hydrogel, a poly(methacrylic acid) gel, a graphene oxide/xonotlite reinforced polyacrylamide (PAAm) gel, a poly(stearyl methacrylate)-polyacrylic acid gel, an annealed PVA-polyacrylic acid hydrogel, supramolecular hydrogels from multiurea linkage segmented copolymers, polyacrylonitrile-PAAm hydrogel, a microsilica reinforced DMA gel, an agar-polyhydroxyethylmethacrylate gel, a polyfacryloyloethyltrimethylammonium chloride hydrogel, a poly(3-(methylacryloylamino) propyl-trimethylammonium chloride hydrogel, a poly(sodium p-styrenbesulfonate) hydrogel, a polyethylene glycol diacrylate hydrogel, a polyethylene glycol hydrogel, or hydrogels composed of a combination of these polymers.

Any of these methods may include mineralizing at least a portion of the nanofiber network adjacent to the surface.

For example, described herein are methods of attaching a hydrogel to a surface of an implant so that the hydrogel is secured to the surface with a shear strength of greater than 1 MPa, the method comprising: securing a dry nanofiber network to the surface, wherein the surface is a porous surface of the implant; rehydrating the nanofiber network; infiltrating the nanofiber network with a hydrogel to form a multiple-network hydrogel on the surface; and forming an outer surface of the hydrogel to a roughness of less than 30 microns. Forming may comprise mechanically polishing an outer surface of the hydrogel. In some examples forming comprises molding an outer surface of the hydrogel. As mentioned above, securing may comprise cementing.

For example, a method of attaching a hydrogel to a surface of an implant so that the hydrogel is secured to the surface with a shear strength of greater than 1 MPa may include: securing a freeze-dried cellulose nanofiber network to the surface, wherein the surface is a porous surface of the implant; rehydrating the freeze-dried cellulose nanofiber network; infiltrating the freeze-dried cellulose nanofiber network with a hydrogel comprising polyvinyl alcohol (PVA) to form a multiple-network hydrogel with the freeze-dried cellulose nanofiber on the porous surface; and forming an outer surface of the hydrogel to a roughness of less than 30 microns. Infiltrating the freeze-dried cellulose nanofiber network with a hydrogel including polyvinyl alcohol (PVA) to form a multiple-network hydrogel may comprise infiltrating with a double-network hydrogel comprising PVA and poly(2-acrylamido-2-methyl-1-propanesulfonic acid sodium salt (PAMPS) to form a triple-network hydrogel with the freeze-dried cellulose nanofiber on the porous surface.

For example, also described herein are methods of attaching a hydrogel to a surface so that the hydrogel is secured to the surface with a shear strength of greater than 1 MPa, the method comprising: cementing a dry nanofiber network to the surface; and infiltrating the nanofiber network with a double-network hydrogel to form a triple-network hydrogel on the surface.

A method of attaching a hydrogel to a surface of an implant (so that the hydrogel is secured to the surface with a shear strength of greater than 1 MPa) may include: cementing a dry nanofiber network to the surface, wherein the surface is a porous surface of the implant; rehydrating the nanofiber network; infiltrating the nanofiber network with a double-network hydrogel to form a triple-network hydrogel on the surface; and mechanically polishing an outer surface of the hydrogel to a roughness of less than 30 microns.

A method of attaching a hydrogel to a surface of an implant so that the hydrogel is secured to the surface with a shear strength of greater than 1 MPa may include: cementing a freeze-dried cellulose nanofiber network to the surface, wherein the surface is a porous surface of the implant; rehydrating the nanofiber network; infiltrating the freeze-dried cellulose nanofiber network with a double-network hydrogel comprising polyvinyl alcohol (PVA), and poly(2-acrylamido-2-methyl-1-propanesulfonic acid sodium salt (PAMPS) to form a triple-network hydrogel on the porous surface; and mechanically polishing an outer surface of the hydrogel to a roughness of less than 30 microns.

Also described herein are methods of mechanically polishing a hydrogel, such as by sanding. Any of the methods described herein may include a step of polishing the hydrogel (e.g., the triple-network hydrogel) by mechanically polishing an outer surface of the hydrogel to a roughness of less than, e.g., 30 microns (e.g., less than 50 microns, less than 40 microns, less than 30 microns, less than 25 microns, less than 20 microns, less than 15 microns, less than 10 microns, etc.). Mechanically polishing may include abrading the hydrogel that is attached to the surface as described herein with a fine grit sandpaper or equivalent.

In general, cementing the dry nanofiber network may include cementing a freeze-dried nanofiber network. For example, the dry nanofiber network may comprise a cellulose nanofiber network, and this cellulose nanofiber network may be freeze dried. In general, any appropriate dry nanofiber network may be used, including one or more of: electrospun polymer nanofibers, poly(vinyl alcohol) (PVA) nanofibers, aramid nanofibers, aramid-PVA nanofibers, wet-spun silk protein nanofiber, chemically crosslinked cellulose nanofiber, or polycaprolactone (PCL) fibers.

The double network hydrogel may be infiltrated into the nanofiber network in steps. For example, if the PVA-PAMPS double network hydrogel is used, the PVA may be infiltrated first; optionally the PVA may be frozen and thawed through one or more cycles before infiltrating the PAMPS to promote crystallization of the PVA, increasing its strength, before infiltrating the PAMPS.

Any of these methods may include rehydrating the nanofiber network. The nanofiber network may be rehydrated before impregnating with the hydrogel or the impregnation may rehydrate the nanofiber network.

In general, infiltrating may include infiltrating the nanofiber network with a double-network hydrogel comprising polyvinyl alcohol (PVA), and poly(2-acrylamido-2-methyl-1-propanesulfonic acid sodium salt (PAMPS) to form a triple-network hydrogel on the porous surface. In some variations infiltrating comprises infiltrating the nanofiber network with a double-network hydrogel comprising one or more of: poly-(N,N'-dimethyl acrylamide) (PDMAAm), copolymers of 1-vinylimidazole and methacrylic acid, amphiphilic triblock copolymers, polyampholyte hydrogels, a PVA-tannic acid hydrogel, a poly(N-acryloyl) glycinamide hydrogel, polyacrylic acid-acrylamide-C18 hydrogel, guanine-boric acid reinforced PDMAAm, polyelectrolyte hydrogels, a poly(acrylonitrile-co-1-vinylimidazole) hydrogel (e.g., a mineralized poly(acrylonitrile-co-1-vinylimidazole) hydrogel), a polyacrylic acid-Fe3+-chitosan hydrogel, a poly(methacrylic acid) gel, a graphene oxide/Xonotlite reinforced polyacrylamide (PAAm) gel, a poly(stearyl methacrylate)-polyacrylic acid gel, an annealed PVA-polyacrylic acid hydrogel, supramolecular hydrogels from multiurea linkage segmented copolymers, polyacrylonitrile-PAAm hydrogel, a microsilica reinforced DMA gel, an agar-polyhydroxyethylmethacrylate gel, a polyfacryloyloethyltrimethylammonium chloride hydrogel, a poly(3-(methylacryloylamino)propyl-trimethylammonium chloride hydrogel, a poly(sodium p-styrenbesulfonate) hydrogel, a polyethylene glycol diacrylate hydrogel, a polyethylene glycol hydrogel, or hydrogels composed of a combination of these polymers.

Any appropriate cement may be used. For example, cementing may include applying an α-TCP cement. In some variations cementing comprises applying a cement comprising one or more of: zinc oxide eugenol, glass ionomer, calcium silicate, polycarboxylate cement, zinc phosphate, resin-based (dental) cements, such as acrylate or methacrylate resin cements, which may contain silicate or other types of fillers in an organic resin matrix (for example, a methacrylate cement such as "RelyX™ Unicem 2 Self-Adhesive Resin Cement," or "RelyX™ Ultimate Adhesive Resin Cement"), and resin-modified glass ionomer cement.

The cementing step may include extending the cement at least 5 microns into the nanofiber network from the first surface (e.g., 6 microns or more, 7 microns or more, 8 microns or more 10 microns or more, 15 microns or more, 20 microns or more, etc.).

In general, cementing may include bonding the nanofiber network without bonding the double-network hydrogel. The cementing step may be completed (and the cement set or dry) before impregnating with the hydrogel.

Any of these methods may include mineralizing at least a portion of the nanofiber network adjacent to the surface. Mineralization may be performed prior to impregnating with the hydrogel or after impregnating (or both). Mineralization may include forming hydroxyapatite on the nanofiber network (or from the nanofiber network). In some variations the cement may mineralize the nanofiber network.

As mentioned above, the surface may be prepared for cementing to the nanofiber network by being porous. For example, cementing the dry nanofiber network to the surface may include cementing the dry nanofiber network to the surface, wherein the surface is greater than 20% porous (e.g., 30% or greater, 40% or greater, 50% or greater, 60% or greater 70% or greater porous, etc.) to a depth of 0.5 mm or greater (e.g., 0.6 mm or greater, 0.7 mm or greater, 0.8 mm or greater, 0.9 mm or greater, 1 mm or greater, etc.).

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 9 is a graph showing the strength of various strategies for attached a hydrogel to a surface.

FIG. 10A is a table comparing the shear strength of different hydrogel attachments to surfaces. In FIG. 10A, abbreviations include: α-TCP (α-tricalcium phosphate); GRFG (gelatin-resorcinol-formaldehyde/glutaraldehyde); NHS (N-hydroxysuccinimide); ASA (aldehyde sodium alginate); AG (amino gelatin); EGK (engineered gelatin-keratin); DOPA (L-3,4-dihydroxyphenylalanine); HPDAC (hyperbranched poly(DOPA-coArg-co-Cys)); HPDAL (Hyperbranched poly[DOPA-co-Argco-Lys acrylamide]); CSS (thiol functionalized chitosan); EPLM (maleimide group modified ε-polylysine); TMPE (trimethylolpropane ethoxylate); TMC (trimethylene carbonate); PEG (poly ethylene glycol); PU (polyurethane); MAP (mussel adhesive protein); DCTA (double-crosslink tissue adhesive. The adhesive strength of α-TCP with stainless steel powder and phosphoserine was tested as described herein. This table includes publications that used a hydrogel or tissue as one of the adherends in a lap shear test.

FIGS. 10B and 10C show graphs of the compressive vs. tensile strength and modulus for BC-PVA-PAMPS (respectively) as well as for other hydrogels.

FIG. 11A shows a two-dimensional (2D) abstraction of the computational framework with the implant in a simulated femur. Physiologically based loading conditions may be applied to the tibia while the femur is fixed. FIG. 11B illustrates implant design features that were evaluated. FIG. 11C (top and bottom) illustrate sensitivity to implant alignment and graft radii.

FIGS. 18A and 18B illustrate examples of a fixture that may be used for aligning forming the materials described herein (e.g., aligning the BC, including a rod, cut BC, and ring clamp) as described herein. FIG. 18A shows a perspective view of the fixture. FIG. 18B shows a sectional view through the fixture.

FIG. 19 is an example of one test fixture that may be used to test searing of cartilage off of bone and/or a hydrogel material off of a test rod, as described herein.

FIG. 20A is a graph illustrating the results for shear testing of the samples shown in FIGS. 21A-21D and 22A-22C (n=3 for all measurements). As shown in FIG. 20B, the difference in the 2 layer and 5 layer BC measurements were statistically significant with a p-value <0.05.

FIG. 21A shows a sample of pig cartilage. FIG. 21B shows an example of a sample of hydrogel without any cement to secure it to the metal substrate. FIG. 21C shows an example of a one-layer cement as described herein. FIG. 21D shows example of a sample in which a clamp was not used to align the BC.

FIGS. 22A-22C show examples of samples test as shown in FIG. 18B, after failure (after the test).

FIG. 23 illustrates one example of a method for attaching a hydrogel (shown here as a BC-PVA-PAMPS hydrogel) to an implant (e.g., a titanium implant) for treatment of osteochondral defects.

FIG. 24 illustrates one example of a clamp (shown as a shape memory alloy clamp in a cartouche shape) as described herein.

FIG. 25 schematically illustrates one method of securing a hydrogel to an implant to have a high shear strength, as described herein.

DETAILED DESCRIPTION

Figure 1A:
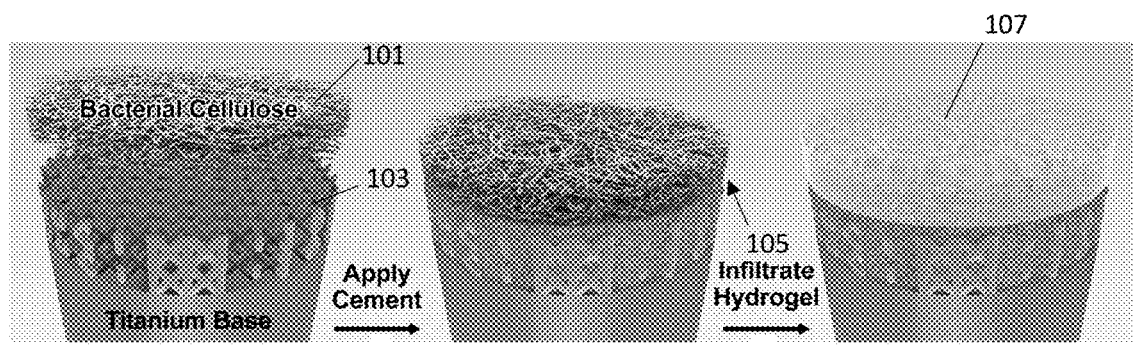
FIG. 1A is an illustration of one example of a process for attachment of a hydrogel to a porous base by a Nanofiber-Enhanced STicking (NEST) method. In this example, a nanofibrous sheet (e.g. Bacterial cellulose) is attached to a surface (e.g., a porous base such as porous titanium) with an adhesive (e.g. α-TCP cement), after which the hydrogel components are infiltrated into the nanofibrous sheet.
Figure 1C:
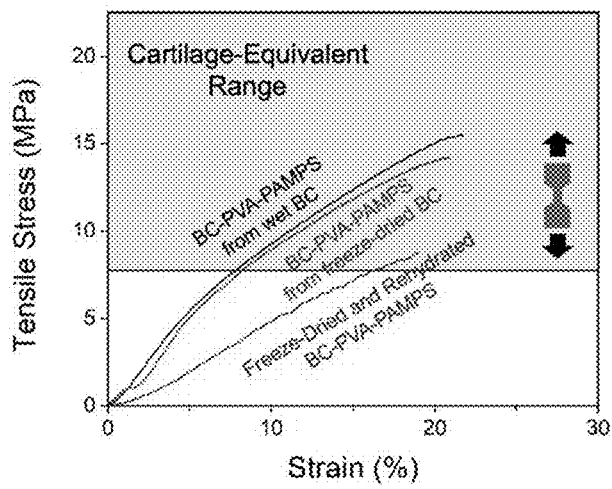
FIG. 1C is a graph of the tensile stress-strain curves comparing BC-PVA-PAMPs hydrogel prepared from wet and freeze-dried BC, as well as freeze-dried and rehydrated BC-PVA-PAMPS.

Hydrogels have been proposed for the long-term repair of cartilage. Repair of a cartilage lesion with a hydrogel requires long-term fixation of the hydrogel in the defect site. Attachment of a hydrogel to a base that allows for integration with bone could enable long-term fixation of the hydrogel, but current methods of forming bonds to hydrogels have less than a tenth of the shear strength of the osteochondral junction. Described herein apparatuses and methods for bonding a hydrogel to a surface (e.g., base) with an adhesive shear strength that is three times larger than has been previously achieved. For convenience, the method of attaching a hydrogel to a surface may be referred to herein as a Nanofiber-Enhanced ATtachment (NEAT) or a Nanofiber-Enhanced STicking (NEST) method or process. In some variations, NEST may include bonding a nanofibrous bacterial cellulose material (e.g., sheet) to a porous base (e.g., surface) with a cement, such as a hydroxyapatite-forming cement, followed by infiltration of the nanofibrous sheet with hydrogel-forming polymeric materials. This approach creates a mineralized nanofiber bond that may mimic the structure of the osteochondral junction, in which collagen nanofibers extend from cartilage into a mineralized region that anchors cartilage to bone.

Articular cartilage lesions, which most often occur in the knee, typically have a limited intrinsic ability to heal, and are associated with joint pain and disability. Common strategies for cartilage restoration, such as microfracture, typically have high failure rates (~50% at 10 years) and prolonged rehabilitation times (12 to 18 months). Implantation of fresh osteochondral allografts can allow immediate weight-bearing and, with a survivorship of 82% at 10 years, is the most successful strategy for treatment of cartilage defects. Unfortunately, the small supply of fresh allografts limits the number of these procedures to around 1% of all cartilage repair surgeries. Decellularized, shelf-stable allografts have very high failure rates (72% in 2 years) characterized by delamination of the articular cartilage in the graft due to collagen degradation. Thus, as mentioned above, there is a need for a cartilage repair method that is widely available, allows immediate weight bearing, has short recovery times, and has low long-term failure rates. Based on the limitations of biological approaches to cartilage restoration, there are ongoing efforts to perform focal joint resurfacing with durable orthopedic materials (e.g. cobalt-chromium alloy) to fill chondral or osteochondral defects. A primary concern with these implants is that they do not match the tribology and mechanical response of native cartilage, resulting in abnormal stress and opposing surface wear causing joint degeneration. Incorrect placement of these implants can lead to severe damage of the opposing cartilage surface. About 20% of patients having focal metallic inlay resurfacing prosthesis have to be converted to arthroplasty after 4 years.

Hydrogels can be created to have a similar stiffness and coefficient of friction as cartilage, thereby addressing concerns related to abnormal stress and wear. However, there is currently no way to secure a hydrogel into a cartilage defect site with the same shear strength as the osteochondral junction (e.g., 7.25±1.35 MPa). One of the strongest tissue adhesives is cyanoacrylate, which has been reported to achieve a lap shear strength of 0.7 MPa between two pieces of cartilage. In contrast, cyanoacrylate bonds nylon to nylon and steel to steel with a shear strength of 2.8 and 7.3 MPa, respectively. The presence of interfacial water in cartilage (cartilage is 60-85% water by weight) hinders the creation of a stronger bond. Thus, removal of water is an important strategy for forming strong bonds to hydrogels.

Described herein are apparatuses, and methods of making and using them, that may address these issues. For example, the method of Nanofiber-Enhanced STicking (NEST), described herein, combines the strategies of water removal and also provides nanofiber mineralization.

FIG. 1 illustrates one example of an apparatus in which a hydrogel has been bonded to an implant surface as described herein. In this example, the hydrogel includes a cross-linked cellulose nanofiber network (e.g., bacteriocellulose, BC), a double network of polyvinyl alcohol (PVA) and polyacrylamide-methyl propyl sulfonic acid (PAMPS). As described herein, the hydrogel may be coupled to the implant surface by first attaching a nanofibrous layer (which may be attached dry) to the surface; the surface may be a porous base. The nanofibrous layer may then be infiltrated with the other hydrogel components. In this way, the nanofibrous portion may be secured with an adhesive or cement that can penetrate secure the porous bacterial cellulose network to the surface and may create an interdigitating bond without the interference of water. For example, in FIG. 1A, the nanofibrous portion is bacterial cellulose 101 that is applied to the prepared surface of the implant (shown in this example as a titanium base, having pores) 103. A cement (e.g., any appropriate medical or dental grade cement may be used) is applied and secures the dry bacterial cellulose to the implant surface. Thereafter the other hydrogel components (e.g., PVA-PAMPS or any other appropriate hydrogel) may be infiltrated into the nanofibrous portion, resulting in the complete hydrogel 107.

Figure 1D:
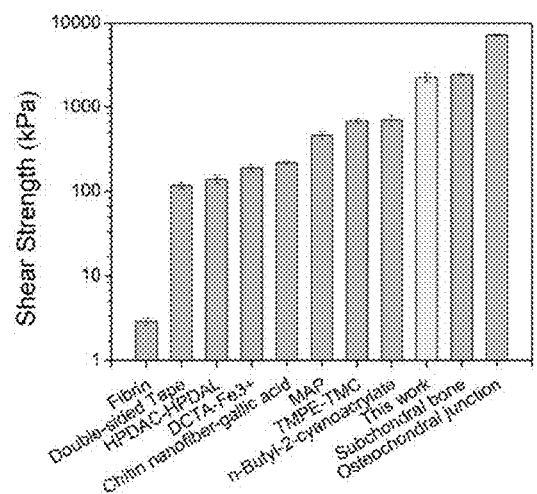
FIG. 1D is a graph comparing the sheer strengths of hydrogels coupled to implant surfaces using the NEST method with an α-TCP cement compared to other hydrogel adhesives and to the osteochondral junction.
Figure 1B:
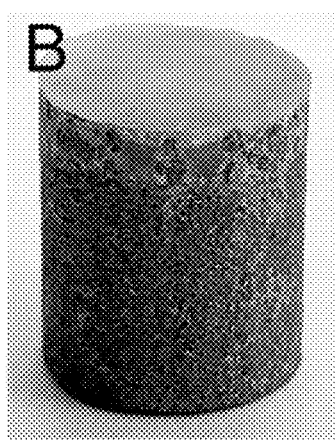
FIG. 1B shows an example of a hydrogel bonded to a titanium plug.

FIG. 1B shows an example of a titanium implant (e.g., plug) to which a BC-PVA-PAMPS hydrogel has been attached, as described herein. In this example, the nanofibrous portion (e.g., BC) of the hydrogel is bonded via a cement to the porous surface of the implant, and the other components of the hydrogel (e.g., PVA-PAMPS) is linked to the nanofibrous portion.

In FIG. 1A-1B and in other examples described herein, the hydrogel including a nanofibrous portion shown is a cartilage-equivalent hydrogel composed of bacterial cellulose (BC), polyvinyl alcohol (PVA), and poly(2-acrylamido-2-methyl-1-propanesulfonic acid sodium salt) (PAMPS), referred to as BC-PVA-PAMPS. As will be described in greater detail below, BC-PVA-PAMPS has excellent properties that are close to cartidge. Further, the BC nanofibers in the hydrogel may provide a source of tensile strength similar to collagen nanofibers in cartilage. However, it should be understood that any appropriate hydrogel including a nanofibrous portion may be used in the methods described herein. See, e.g., U.S. patent application Ser. No. 16/332,574, filed on Nov. 7, 2018, titled "Triple-network hydrogel implants for repair of cartilage", and herein incorporated by reference in its entirety.

In general, the nanofibrous portion may be combined with the other hydrogel components when the nanofibrous portion is wet or dry. Most previously described hydrogel (including "triple network" hydrogels) are prepared from wet nanofibrous portions. As described herein the nanofibrous portion may instead by prepared dry, including by freeze-drying. For example, BC may be freeze-dried and infiltrated with PVA and PAMPS to create a hydrogel with nearly the same tensile strength (12.37±3.83 MPa) as one that is not freeze dried (13.42±3.86 MPa). See, e.g., FIG. 1C.

Figure 2:
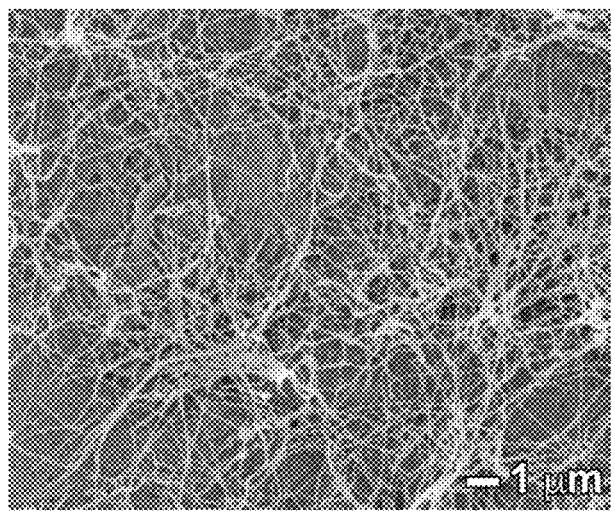
FIG. 2 shows an example of a SEM image of the surface of a freeze-dried bacterial cellulose sheet.

As shown, the tensile strength of hydrogels prepared by infiltration of wet or freeze-dried BC are well within the range of tensile strengths reported for human cartilage (8.1-40 MPa). In contrast, if the full BC-PVA-PAMPS hydrogel is freeze-dried, the tensile strength is only 9.62±2.63 MPa. Thus, the nanofibrous BC can accommodate the formation of ice crystals by fiber displacement without fiber fracture, whereas the molecularly cross-linked hydrogel network may be irreversibly damaged by ice crystal formation. FIG. 2 is a scanning electron microscope (SEM) image of the surface of a freeze-dried piece of BC, which shows that it consists of many nanoscale fibers that present a large surface area for attachment with an adhesive.

FIG. 1D is a graph showing a comparison between the maximum adhesive shear strength achieved by the methods described herein (e.g., the NEST method) compared to previous work. See also, FIGS. 6 and 9. The apparatuses described herein, in which the nanofibers (e.g., BC nanofibers) are bonded with a cement (e.g., a hydroxyapatite-forming cement) may achieve an adhesive shear strength of 2.28±0.27 MPa, a three-fold increase over that previously described, and mimicking the osteochondral junction. Although this value is slightly lower than the shear strength reported for the human osteochondral junction (e.g., 7.25±1.35 MPa), it is similar to the shear strength reported for the bovine osteochondral junction (e.g., 2.6±0.58 MPa) and human subchondral bone (e.g., 2.45±0.85).

As mentioned above, any appropriate cement may be used to adhere the nanofibrous portion of the hydrogel to the surface. In some variation the cement is α-tricalcium phosphate (α-TCP), a hydroxyapatite-forming cement that may be used for attachment of the hydrogel due to its biocompatibility, osteoconductivity, and shear strength, which may exceed that of cyanoacrylate. By itself, α-TCP does not act as an adhesive. Thus, the addition of 10 wt % phosphoserine (PPS), a component of sandcastle worm glue (to promote adhesion) was also tested. In addition, Hydroxyapatite is brittle and benefits from reinforcement, so the addition of 12 wt % Stainless-steel powder (SSP) with an average particle size of 150 µm to hinder crack propagation was also tested.

For example, adhesive shear testing, including testing of the cement by itself, was examined using a dry cement mixture consisting of 0.040 g PPS, 0.312 g of α-TCP and 0.048 g of SSP, placed into a small dish, 0.140 ml of water was added, and the powder was rapidly mixed with the water. Powders were also created without PPS or SSP to examine the effects of these additives. Approximately 0.150 ml of the wet cement mixture was added on top of a porous titanium plug in a metal die with an inner diameter of 6 mm. The plug consisted of a titanium alloy (Ti6Al4V) topped with a 1-mm-thick layer of 3D printed struts with a porosity of 70%. Thus, in any of these variations the implant surface may be a porous surface; in some variations the porous surface 103 include a plurality of struts as shown in FIG. 1A. In this example the rendering of the strut structure was designed in a computer aided design (CAD) file and printed using 3D printing. The titanium plug shown is 6 mm in diameter and 6.35 mm in height and was used for testing.

Figure 3A:
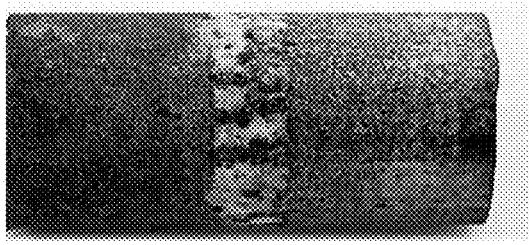
FIGS. 3A-3B show an example of an α-TCP cement sample before (FIG. 3A) and after (FIG>3B) shear testing.

To test the wet or dry (e.g., freeze-dried) nanofibrous portion, a second titanium plug was placed into the die with the porous layer in contact with the wet cement, and the sandwich structure was pressed together for 1 hour at 250 MPa. Samples were also made without the application of pressure to test the effect of this step on shear strength. The application of pressure has previously been demonstrated to reduce the porosity of calcium phosphate cements, thereby improving their compression and flexural strength, but the effect of pressure on the adhesive shear strength of an α-TCP cement has not been reported. The sample was placed into water at 85° C. for at least 24 hours to facilitate the transformation of α-TCP into hydroxyapatite and was stored in water until just prior to shear testing. FIG. 3A shows an image of the sandwich structure in which the α-TCP cement bonds two titanium plugs, each with a 1-mm-thick layer of struts with a porosity of 70%.

Shear testing was performed on a Test Resources 830LE63 Axial Torsion Test Machine equipped with a 100 lb. load cell and a custom-made shear testing fixture. A crosshead displacement rate of 2 mm/min was used for all the measurements. The plugs were placed in the fixture so that the interface between the plugs was centered in the gap between the L-shaped metal plates that make up the fixture.

Figure 3B:
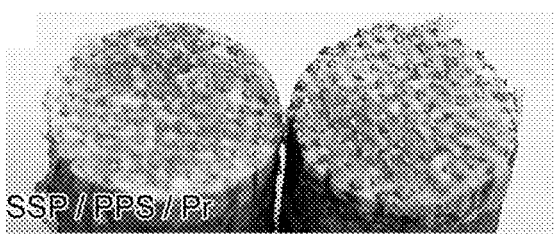

FIG. 3B shows a cement fracture surface after shear testing, indicating cohesive failure. This particular sample contained SSP, PPS, and was pressed, but all cement samples exhibited a similar cohesive fracture surface. A previous study of a PPS-containing α-TCP cement demonstrated that failure can be partially adhesive for bonding smooth titanium plugs but becomes cohesive when the cementitious bond is made between porous titanium surfaces.

Figure 3C:
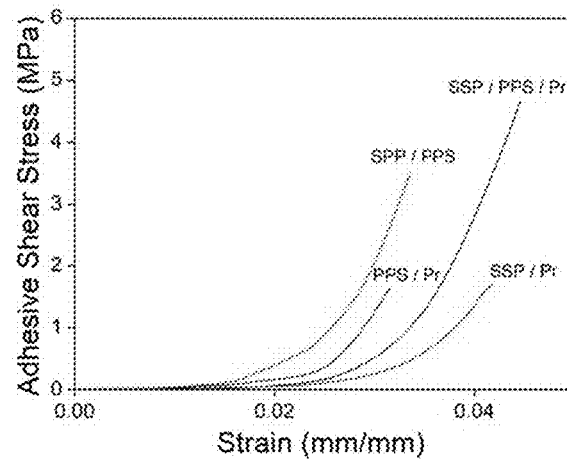
FIG. 3C is a graph showing the results of testing, showing stress-strain curves for different cement compositions.
Figure 3D:
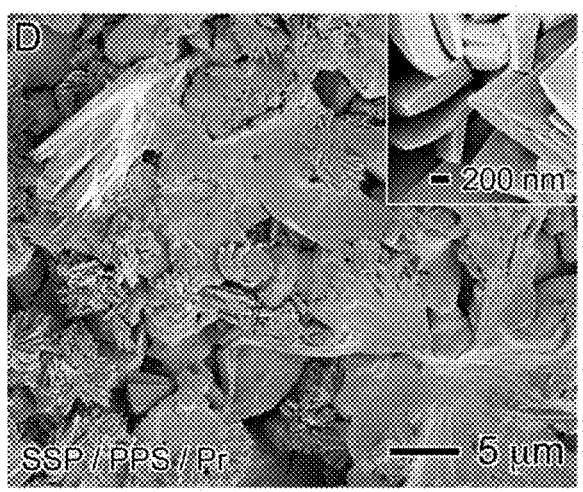
FIG. 3D is an SEM image of the fracture surface for a sample containing SSP and PPS that was pressed at 250 MPa.
Figure 3E:
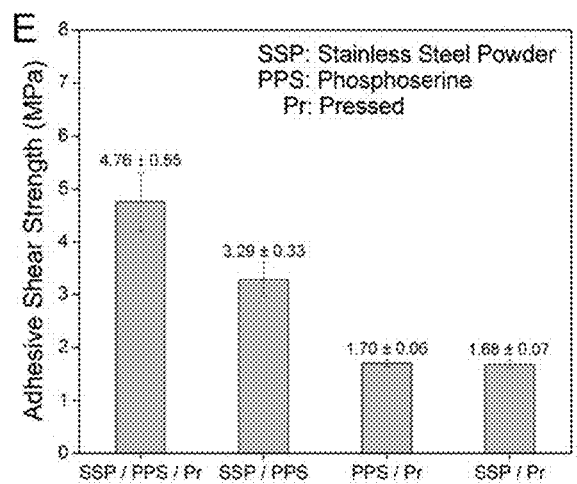
FIG. 3E graphically illustrates the effect of composition and pressing on adhesive shear strength (n=3).
Figure 3F:
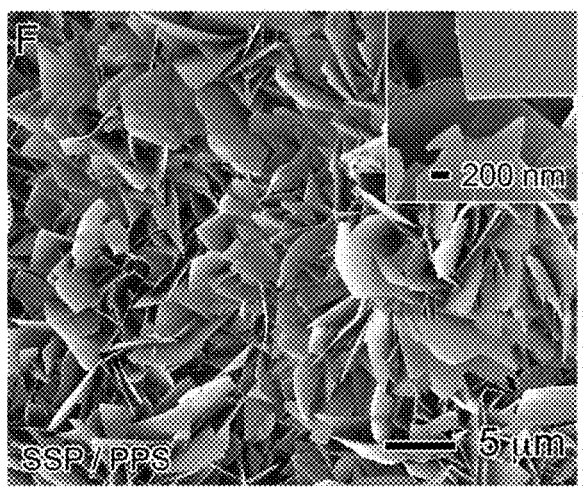
FIG. 3F is an SEM image of the fracture surface for the sample made with SSP and PPS without pressing.

FIG. 3C shows typical stress strain curves for shear testing of cements with different compositions, and FIG. 3D shows the average and standard deviation of the strength for three samples of each composition. The cement composition with the highest adhesive shear strength (4.76±0.55 MPa) was pressed at 250 MPa and contained both SSP and PPS, in addition to the α-TCP cement. Without the pressing step, the adhesive shear strength decreased to 3.29±0.33 MPa. The scanning electron microscopy (SEM) image of the fracture surface for the pressed sample in FIG. 3D shows the hydroxyapatite crystals at the fracture surface were thicker than the flake-like hydroxyapatite crystals that grew in samples that were not pressed (FIG. 3F). Both surfaces differ substantially in morphology from spheroidal α-TCP cement particles. Thus the application of pressure not only changes the porosity but also the crystal morphology of the hydroxyapatite in the cement, with the stronger sample consisting of a thicker hydroxyapatite crystal morphology.

Without PPS, the adhesive shear strength decreased to 1.68±0.07 MPa. Without the SSP, the adhesive shear strength decreased to 1.70±0.06 MPa. Thus, SSP, PPS, and mechanical pressing may all maximize the adhesive shear strength of the cement. Thus, any of the apparatuses and methods described herein may include a cement (securing the nanofibrous portion to the surface of the implant, such as a porous base) that includes a powder (e.g., stainless steel powder, SSP), and/or an additional adhesive (e.g., 10 wt % phosphoserine (PPS)), and or may be pressed (e.g., mechanically pressed).

Figure 3G:
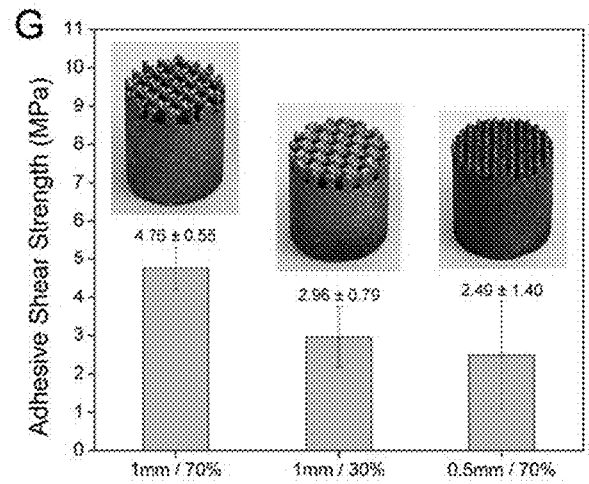
FIG. 3G is a graph showing the effect of the strut structure on adhesive shear strength (n=3).

As mentioned above, any of these implant surfaces may include a porous structure. The porosity of the implant surface may be, e.g., between 10% porous and 90% porous, e.g., between 30% porous and 90% porous, between 55% porous and 95% porous, between 65% porous and 85% porous, etc.). The depth of the pores may also be varied. For example, the surface may be porous to a depth of between 0.1 mm and 5 mm, between 0.2 mm to 3 mm, between 0.5 mm to 2 mm (e.g., 0.2 mm or greater, 0.3 mm or greater, 0.5 mm or greater, 0.75 mm or greater, 1 mm or greater, 1.5 mm or greater, etc.). FIG. 3G illustrates examples of porous structure of the 3D printed titanium layer and show the effect of porosity on the shear strength between two titanium plugs. In this example, two changes were made: decreasing the porosity from 70% to 30% and decreasing the thickness of the strut layer (forming the pores) from 1 mm to 0.5 mm. As shown in FIG. 3F, both changes led to a decrease in the adhesive shear strength. Thus, it may be preferable to have a porosity in which at the surface to be coupled to the hydrogel has a porosity that extends at least 1 mm or thicker and has a porosity of 70% or more.

Figure 4A:
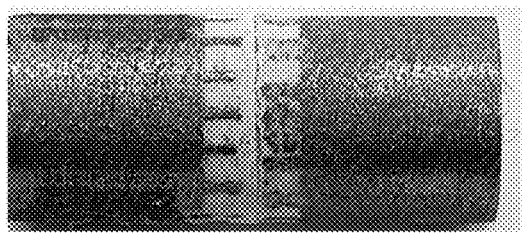
FIG. 4A shows an example of an image of sample for testing hydrogel-cement adhesive shear strength before shear testing.

Similar testing was used to examine the strength of the hydrogel attachment to an implant surface. For example, testing was performed with a cement (e.g., a cement composed of 10 wt % PPS, 78 wt % α-TCP and 12 wt % SSP) coupled to a nanofibrous portion of the hydrogel before impregnating the nanofibrous portion with the rest of the hydrogel (e.g., PVA-PAMPS). The cement mixture consisting of 0.080 g PPS, 0.624 g of α-TCP and 0.096 g of SSP was placed into a small dish, 0.280 ml of water was added, and the powder was rapidly mixed with the power. Then 0.150 ml of the wet cement mixture was added on top of the porous titanium plug in the die. A nanofibrous material (e.g., a BC sheet) was then placed on top of the cement in the die, and an additional 0.150 ml of the wet cement mixture was added on top of the BC sheet. A second porous titanium plug was then placed on top of the BC sheet in the die to create a sandwich structure. The sandwich structure was pressed for 1 hour at 250 MPa. The sample was placed into water at 85° C. for 24 hours to facilitate the transformation of α-TCP into hydroxyapatite. The sample was then placed into a hydrothermal reactor with a mixture of PVA (40 wt. %) and DI water (60 wt. %) to infiltrate PVA into the BC layer. The sample was frozen at −78° C. and thawed to room temperature to further increase the strength of the PVA hydrogel. The sample was then soaked in a solution containing AMPS, (30 wt. %) cross-linker (N,N'-Methylenebisacrylamide, 60 mM), and heat initiator (12959, 50 mM) for 24 hours. The hydrogel was heat cured at 60° C. for 8 hours and the sample was soaked in DI water for at least 24 hours. An image of the finished sample is shown in FIG. 4A.

Figure 4B:
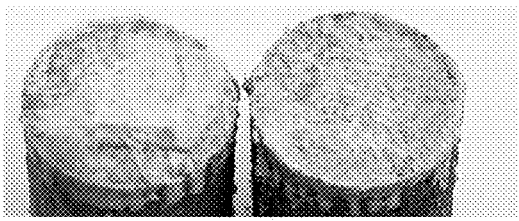
FIG. 4B shows the sample of FIG. 4A after shear testing.

FIG. 4B shows an image of a fracture surface after adhesive shear testing. For the fracture surface between the two titanium plugs in FIG. 3B, the titanium prongs are visible through the cement, suggesting that the metal prongs were in contact prior to fracture. In contrast, for the fracture surface with the BC-PVA-PAMPS hydrogel between the titanium plugs in FIG. 4B, the titanium prongs are not visible. Instead the white, fibrous BC layer is covering the prongs on the right plug, and the hydrogel infiltrated into the remaining BC is covering the prongs on the left. This shows that the hydrogel completely penetrated through the BC layer in between the plugs. This fracture surface, as well as other similar fracture surfaces not shown, also suggests that fracture took place close to the interface between the hydrogel and cement in the BC layer. This may be due to stress concentration at the interface between the relatively soft hydrogel and hard cement. Previous studies of shear fracture of the osteochondral junction similarly show that fracture of the osteochondral junction occurs at the tidemark, i.e., the border between cartilage and mineralized cartilage, presumably due to stress concentration at this interface.

Figure 4C:
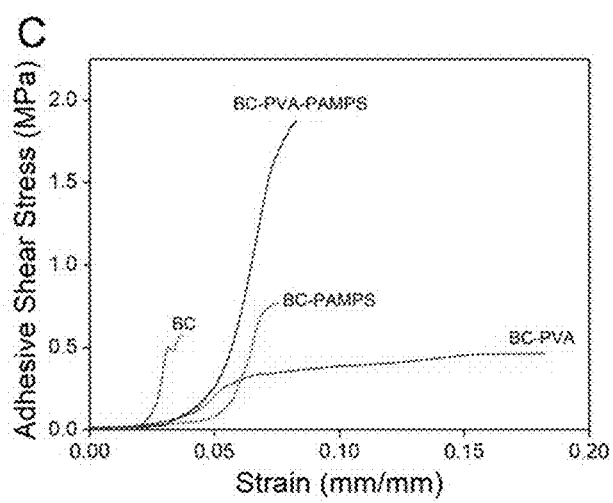
FIG. 4C is a graph showing typical stress strain curves for hydrogels with different compositions.
Figure 4D:
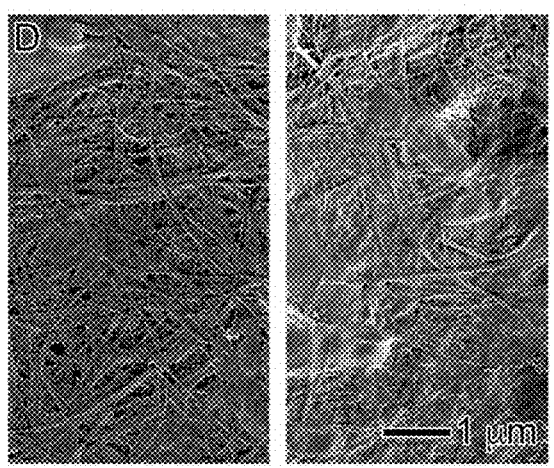
FIG. 4D is an SEM images of the fracture surfaces in FIG. 4B.

FIG. 4D shows an example of SEM images of the left and right fracture surfaces in FIG. 3B, showing the presence of BC and hydrogel on both surfaces. Hydroxyapatite was not observed at the fracture surface after hydrogel infiltration.

Figure 4E:
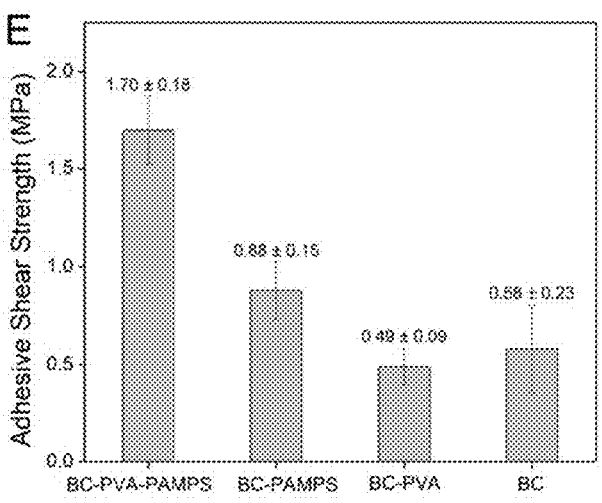
FIG. 4E is a graph showing adhesive shear strength and standard deviations for different hydrogel compositions (n=3).
Figure 4F:
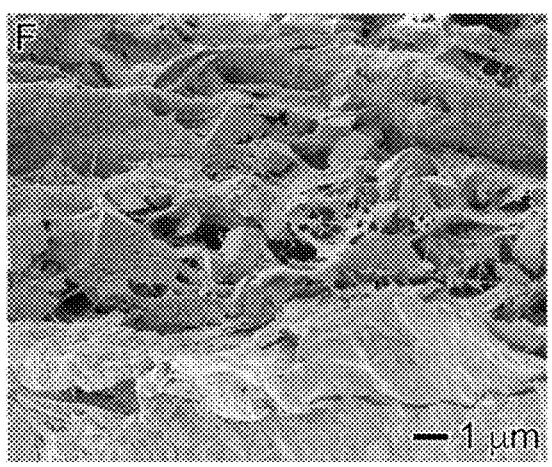
FIG. 4F is a cross-sectional SEM image of hydroxyapatite mineralizing the BC nanofibers.
Figure 5:
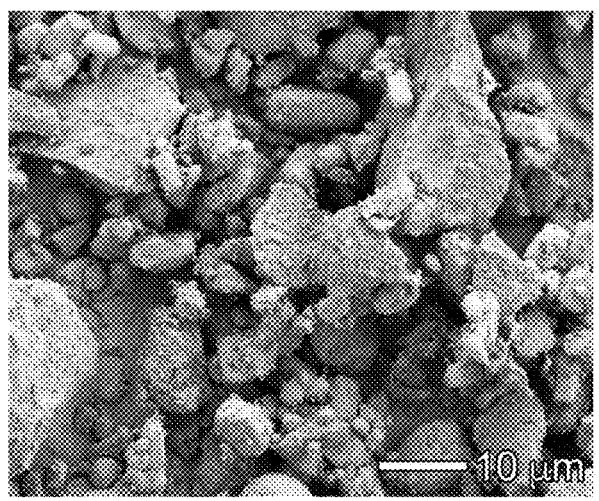
FIG. 5 shows an example of a scanning electron microscopy (SEM) image of α-TCP powder.

FIG. 4C shows typical stress-strain curves for different hydrogel compositions, including BC-PVA-PAMPS, BC-PAMPS, and BC-PVA, as compared to just BC. FIG. 4E shows the adhesive shear strength and standard deviation of three samples for each condition. With BC only in between the two titanium plugs the adhesive shear strength was 0.58±0.23 MPa eight times lower than the shear strength of the cement without the BC. This again indicates the cement is attached to the BC layer rather than forming a continuous bond through the BC. In some variations the cement may have particles having an average size that is larger than the pores of the nanofibrous portion. For example, the size of the α-TCP cement particles is 6.6±4.9 µm, which is much larger than the pores in the BC layer. See, e.g., FIG. 5, an SEM showing the cement particles. Therefore, even though a large pressure is applied to the sandwich structure, the cement (e.g., α-TCP) particles will not completely penetrate through the BC layer. This was confirmed experimentally; when a nanofibrous material (e.g., BC) was pressed into a cement at 250 MPa, and placed in water at 85° C. for 24 hours to form hydroxyapatite the interface between the nanofibrous material and the cement (e.g., the BC-cement interface) shows hydroxyapatite crystals up to about 10 microns from the cement-BC interface, with their frequency decreasing with increasing distance from the interface. See, e.g., FIG. 4F. This interface shows that the nanofibrous material is indeed mineralized by the hydroxyapatite. The hydroxyapatite did not extend into the nanofibrous portion beyond about 10 microns. The nanofibrous material present 40 microns from the interface with the cement was completely devoid of hydroxyapatite.

Infiltration of PVA into the BC layer increased the strain at failure, but not the adhesive shear strength. Infiltration of PAMPS into the BC layer also did not significantly increase the strength and led to a smaller increase in the strain at failure than PVA due to the more brittle nature of the PAMPS hydrogel. However, infiltration of both PVA and PAMPS into the BC layer leads to an increase in the adhesive shear strength to 1.70±0.18 MPa, an increase of almost 300%. These results indicate the hydrogel components are penetrating into the BC layer and that both components may help achieve a larger adhesive shear strength than BC alone.

Figure 4G:
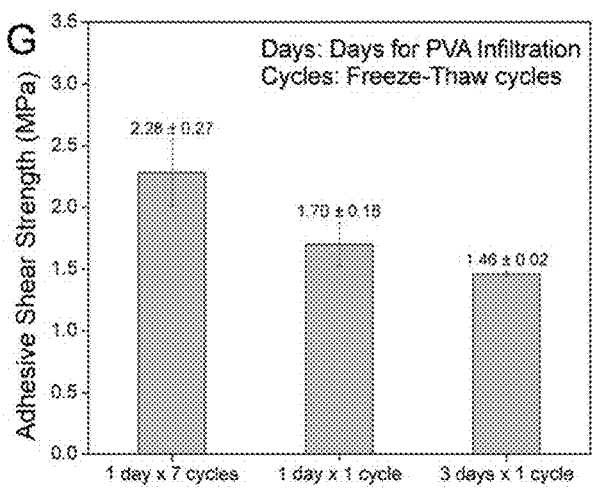
FIG. 4G is a graph showing the effect of the hydrogel processing on adhesive shear strength (n=3).

In some variations the adhesive shear strength may be further improved by performing multiple freeze-thaw cycles on the hydrogel. It has previously been shown that multiple freeze-thaw cycles increases the tensile strength of PVA film. Seven cycles of freezing and thawing was applied to the PVA after infiltration into the BC, and before infiltration of the PAMPS. Multiple cycles of freezing and thawing increase the adhesive shear strength to 2.28±0.27 MPa, as shown in FIG. 4G. This is within the range of the shear strength between cartilage and subchondral bone (2.45±0.85 MPa), indicating the strength of this interface may be sufficient for attachment of the hydrogel to a porous titanium implant that allows for bone ingrowth.

Different times for diffusing the PVA into the BC layer were examined, for example, by heating in the hydrothermal reactor for three days instead of one day at 110° C. This processing change did not improve performance, indicating that the PVA is fully diffused into the BC layer within 24 hours.

As described herein, the NEST methods may result in apparatuses in which the nanofibrous portion is cemented to the porous substrate of the implant, and the other components of the hydrogel are impregnated within the nanofibrous portion. These methods are made possible by the removal of interfacial water and nanofiber mineralization to create a bond to a hydrogel that is at least three times stronger that is currently otherwise achievable. In the examples described above, an α-TCP cement containing phosphoserine for adhesion and stainless steel micropowder for reinforcement was used. The cement undergoes hydrolysis to form hydroxyapatite flakes that bond with a nanofibrous sheet of BC. This bond is strengthened further after infiltration of PVA and PAMPS into the BC sheet, resulting in nanofiber-mediated attachment between the hydrogel and the cement. These results show strong bonds to hydrogels can be achieved by mimicking the nanoscale structure of the osteochondral junction, namely the mineralization of the collagen nanofibers that give cartilage its tensile strength. This strategy may prove useful for creating hydrogel-capped titanium implants for cartilage resurfacing, in which the porous titanium base facilitates osseointegration and long-term fixation.

Figure 6:
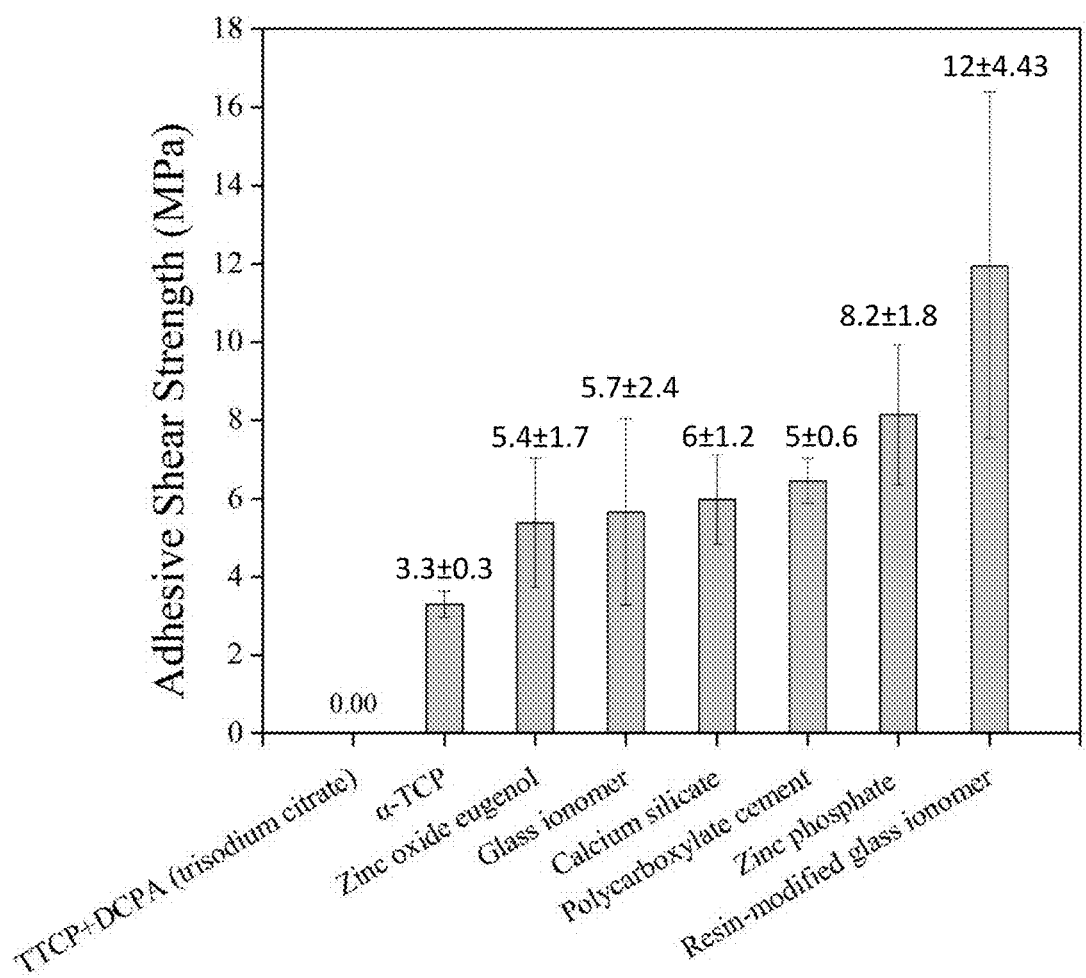
FIG. 6 is a graph illustrating the strengths of different biocompatible cements between two porous titanium plugs.

As mentioned above, any appropriate cement may be used. Although an α-TCP cement was used in the examples described above, other examples of cements are shown in FIG. 6, along with their relative adhesive shear strengths. A number of other biocompatible cements were also tested for their ability to adhere two titanium plugs together. FIG. 6 shows that most of these cements, including Zinc oxide eugenol (Dental Care Kit), glass ionomer (Primal Dental), calcium silicate (Hartline), polycarboxylate cement (Dentonics), zinc phosphate (Primal Dental), resin-based (dental) cements, such as acrylate or methacrylate resin cements, which may contain silicate or other types of fillers in an organic resin matrix (for example, a methacrylate cement such as "RelyX™ Unicem 2 Self-Adhesive Resin Cement," or "RelyX™ Ultimate Adhesive Resin Cement") and resin-modified glass ionomer cement (3M ESPE) all exhibit higher shear strengths than the α-TCP cement. Note that these samples were not pressed, leading to a lower strength for the α-TCP. These adhesives may be used in place of the α-TCP to attach the hydrogel to an implant, including to a porous titanium base, with a higher shear strength. Besides these cements, other cements, adhesive resins, and their composites, such as those commonly used in dentistry, may also be suitable for bonding the nanofibrous portion of the hydrogel (e.g., freeze-dried BC) to the titanium substrate.

As mentioned, any appropriate nanofibrous network may be used, including, but not limited to nanofibrous bacterial cellulose. Other nanofibrous networks may include electrospun polymer nanofibers such as poly(vinyl alcohol) (PVA) nanofibers, aramid nanofibers (e.g., aramid-PVA nanofibers), wet-spun silk protein nanofiber, chemically cross-linked cellulose nanofiber, or polycaprolactone fibers (e.g., 3D woven PCL fibers). In addition, any appropriate double network hydrogels may be used, including but not limited to PVA and PAMPS. For example, other hydrogel-forming polymers may include poly-(N,N'-dimethyl acrylamide) (PDMAAm), copolymers of 1-vinylimidazole and methacrylic acid, double-network hydrogels based on amphiphilic triblock copolymers, polyampholyte hydrogels, a PVA-tannic acid hydrogel, a poly(N-acryloyl) glycinamide hydrogel, polyacrylic acid-acrylamide-C18 hydrogel, guanine-boric acid reinforced PDMAAm, polyelectrolyte hydrogels, a poly(acrylonitrile-co-1-vinylimidazole) hydrogel (e.g., a mineralized poly(acrylonitrile-co-1-vinylimidazole) hydrogel), a polyacrylic acid-$Fe^{3+}$-chitosan hydrogel, a poly(methacrylic acid) gel, a graphene oxide/Xonotlite reinforced polyacrylamide (PAAm) gel, a poly(stearyl methacrylate)-polyacrylic acid gel, an annealed PVA-polyacrylic acid hydrogel, supramolecular hydrogels from multiurea linkage segmented copolymers, polyacrylonitrile-PAAm hydrogel, a microsilica reinforced DMA gel, an agar-polyhydroxyethylmethacrylate gel, a polyfacryloyloethyltrimethylammonium chloride hydrogel, a poly(3-(methylacryloylamino)propyl-trimethylammonium chloride hydrogel, a poly(sodium p-styrenbesulfonate) hydrogel, a polyethylene glycol diacrylate hydrogel, a polyethylene glycol hydrogel, or hydrogels composed of a combination of these polymers.

The implants described herein may be formed of any appropriate material, including, but not limited to titanium and stainless steel. For example, a hydrogel may be attached as described herein to an implant surface (e.g., base, including a porous base) that is formed of a stainless steel alloy (e.g. 316), other titanium alloys, Co—Cr alloys, tantalum, Gold, Niobium, bone, Al oxide, Zr oxide, hydroxyapatite, Tricalcium phosphate, calcium sodium phosphosilicate (Bio glass), poly(methyl methacrylate), polyether ether ketone, polyethylene, polyamide, polyurethane, polytetrafluoroethylene, or other materials used for making implants.

Figure 8:
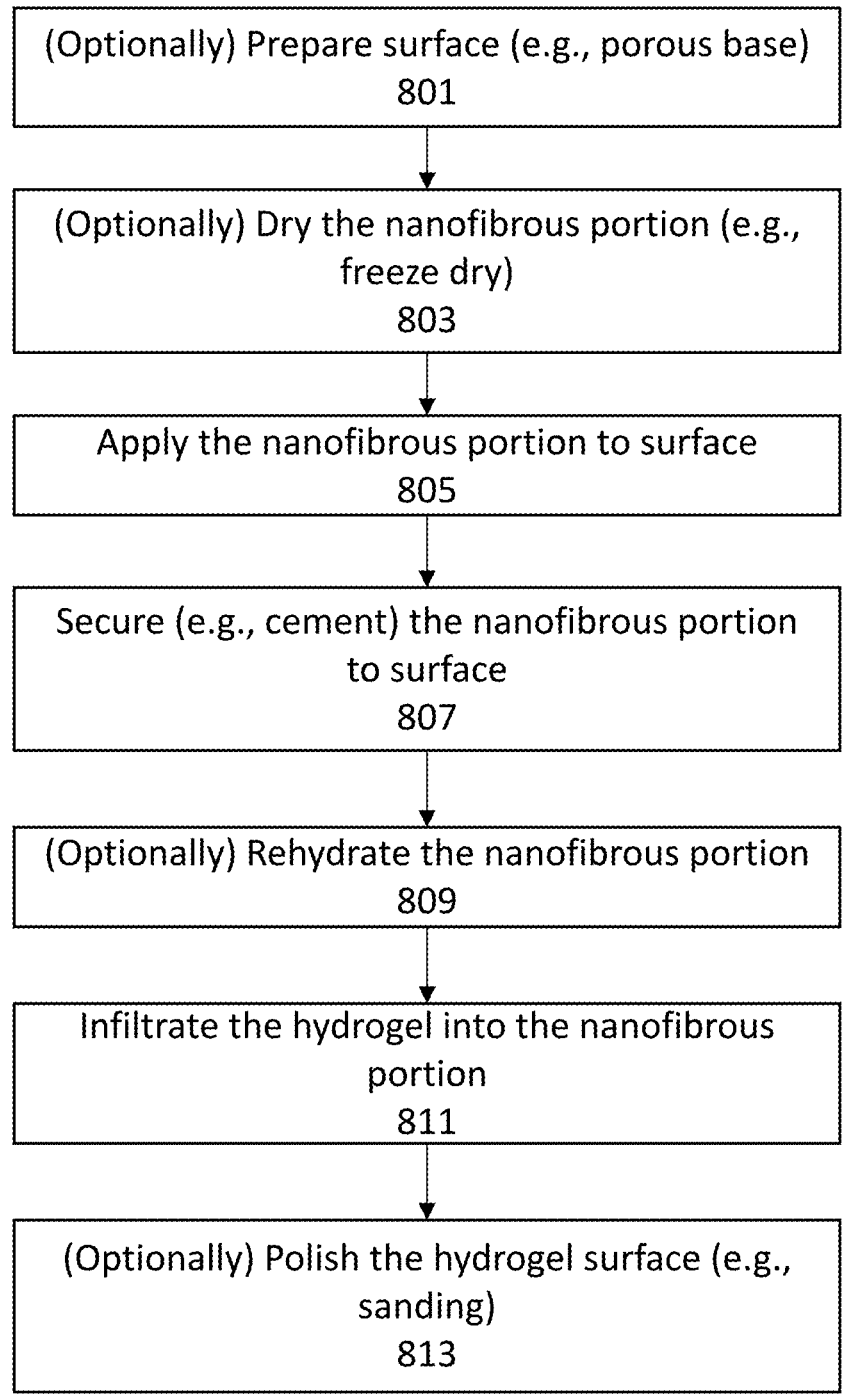
FIG. 8 illustrates one method of forming and attaching a hydrogel surface as described herein.

FIG. 8 illustrates one example of a method of making an apparatus as described herein. As mentioned, this method may be considered a variation of the NEST method described above. In FIG. 8, the surface to which the hydrogel is to be attached, e.g., an implant surface, may optionally be prepared 801. For example, the surface may be made porous. The porosity may be at least 0.5 mm deep (e.g., 1 mm deep or deeper). The porosity may be described as the percent porosity (e.g., between 10% and 90% porous, between 20% and 90%, greater than 30%, greater than 40%, greater than 50%, etc.).

The nanofibrous portion may then be prepared for attachment to the surface 803. For example, the nanofibrous portion dried (e.g., freeze dried). In general, the nanofibrous portion may be applied dry or substantially dry, to the surface 805. The nanofibrous portion may then be cemented to the surface 807. In some variations the cement may be applied to the surface before the nanofibrous portion is applied and/or the cement may be applied onto the nanofibrous portion on the surface. In some variations the cement may be applied to the nanofibrous portion prior to attaching to the surface.

The cement may be applied to dry (e.g., for a predetermined time, e.g., 1 hour, 2 hours, 3 hours, 6 hours, 12 hours, 24 hours, etc.) at a drying temperature (e.g., room temperature, 30 degrees, etc.). Once dried, the nanofibrous portion that is cemented to the surface may optionally be rehydrated 809, e.g., by the addition of an aqueous solution.

The nanofibrous portion may then be infiltrated by the other components of the hydrogel 811. For example, a double-network hydrogel (e.g., PVA-PAMPS hydrogel) may be impregnated into the nanofibrous portion that is cemented onto the surface.

As mentioned above, any of these and apparatuses may include a hydrogel having a surface that is substantial smooth and/or is shaped in a predetermined configuration, such as (but not limited to) concave, convex, saddle-shaped, etc. For example, any of these apparatuses (e.g., implants) may have a surface roughness that is less than 30 microns. In some cases the surface may be formed smooth by molding. In some cases the surface may be formed smooth by polishing or sanding. For example, once the additional hydrogel components have formed the network (e.g., the nanofibrous-reinforced network, such as a triple network), the hydrogel coating may optionally be finished by polishing; in particular, the surface may be sanded to polish to a roughness of less than 30 microns. Polishing may be performed by sanding (e.g., using a fine grit sanding surface, such as a 600, 400, 320, etc. grit).

The methods and apparatuses (e.g., devices, systems, etc. including in particular implants) described herein may be used to form an attachment between a hydrogel and a substrate, including (but not limited to) a hydrogel and a metal substrate for part of a medical implant. These methods and apparatuses may include a hydrogel that includes, as part of the hydrogel, a bacterial cellulose. For example, the hydrogel may be a triple network hydrogel that includes a bacterial cellulose material. In general, the bacterial cellulose within the hydrogel may be oriented as described herein so that the bacterial cellulose fibers are generally oriented perpendicular to the substrate to which they are applied. The substrate may be a porous substrate, such as a porous metal (e.g., titanium).

In some examples the apparatuses described herein may form part of a surgical implant for treating a defect, such as an osteochondral defect. For example, a surgical implant may include a surface that is covered in a hydrogel; this surface may act an interface between one or more other body regions, including hard tissues, such as bone and cartilage. Repair of a cartilage lesion with a hydrogel may benefit from long-term fixation of the hydrogel in the defect site. Attachment of a hydrogel to a base (substrate) that allows for integration with bone could enable long-term fixation of the hydrogel, but current methods of forming bonds to hydrogels have less than a tenth of the shear strength of the osteochondral junction. The apparatuses and methods described herein may include bonding a hydrogel to a surface (e.g., base) with a shear strength that is many times larger than has been previously achieved.

Articular cartilage lesions, which most often occur in the knee, typically have a limited intrinsic ability to heal, and are associated with joint pain and disability. The shear strength of an attachment between human cartilage and bone has been reported to be about 7.25±1.35 MPa when tested at the osteochondral junction, or about 2.45±0.85 Mpa when tested at the level of the subchondral bone (both were tested at a shear rate of 0.5 mm/min). This difference in shear strength may explain why subchondral bone fractures are more common than removal of cartilage from bone. Others have measured the shear strength of the mature bovine osteochondral junction to be 2.6±0.58 MPa, albeit at a higher shear rate (38 mm/min). In comparison, cyanoacrylate ("Super Glue") bonds cartilage with a shear strength of 0.7 MPa. The high shear strength of the osteochondral junction may be attributed to the way in which the collagen nanofibers, which give cartilage its high tensile strength, are mineralized and anchored to the surface of bone with hydroxyapatite.

One way to increase the shear strength (e.g., to 2.28±0.27 MPa) for a hydrogel on titanium may be achieved by first bonding freeze-dried bacterial cellulose (BC, which consists of a network of celluose nanofibers) to titanium with an α-tricalcium phosphate (α-TCP) cement, follwed by infiltration of polyvinyl alcohol (PVA) and poly(2-acrylamido-2-methyl-1-propanesulfonic acid (PAMPS) into the bacterial cellulose to create a BC-PVA-PAMPS hydrogel. This approach, developed as part of the same work described herein, may be referred to as Nanofiber-Enhanced STicking (NEST). Although the shear strength achieved with NEST represented a three-fold increase over the state-of-the-art, described herein are further improvements that may allow the highest values of the shear strengths (e.g., 7.25±1.35 MPa or more) similar to those reported for the human osteochondral junction. In addition, the methods and apparatuses described herein may be directly compared with the shear strength of cartilage with the same test fixture.

The methods and apparatuses described herein may increase the adhesive shear strength between a hydrogel and a substrate (e.g., a metal substrate) so that it matches the shear strength of attachment between cartilage and bone in the same test fixture. To show this, several alternative cements were compared to α-TCP. Although these alternative cements increased the shear strength of attachment between porous titanium plugs, they did not increase the adhesive shear strength between the BC-PVA-PAMPS hydrogel and porous titanium. The work described herein, for the first time, proposed and examines the hypothesis that the shear strength of the hydrogel on titanium is limited by delamination of the cellulose nanofiber layers, which are typically oriented parallel to the direction of the applied shear force. This hypothesis was tested by orienting the cellulose nanofibers perpendicular to the substrate (and therefore oriented perpendicular to the direction of the applied shear force), e.g., by wrapping the BC layer over the sides of the cylindrical metal plug. The bacterial cellulose (BC) layers and the resulting hydrogel were secured in place, e.g., with a shape memory alloy clamp. This change in nanofiber orientation increased the shear strength of attachment to be equivalent to the porcine osteochondral junction in the same test fixture. In this orientation, the shear strength of attachment increased with the number of BC layers, which increased the force required to fracture the hydrogel at the periphery of the plug. This new method of hydrogel attachment will allow the creation of orthopedic devices with surfaces that mimic the properties of cartilage.

EXAMPLES

A hydrogel may be attached to a titanium base with the strength and fatigue of cartilage on bone. Current strategies for attachment of a hydrogel to a substrate are weaker than the osteochondral junction by a factor of ten. The methods and apparatuses described herein may achieve an attachment strength between a hydrogel and a porous substrate equivalent to the osteochondral junction. Thus a hydrogel may be attached to a titanium base with the shear strength and fatigue strength of the osteochondral junction.

A hydrogel-capped implant may be configured so as to promote osseointegration while minimizing abnormal stresses that might arise due to slight imperfections in the placement of the implant during surgery. The hydrogel may be attached to a porous titanium base with the strength of the osteochondral junction. These methods and apparatuses may allow fabrication of a hydrogel-capped implant for implantation, enabling hydrogel-capped implants for rapid repair of cartilage lesions, thereby preventing the abnormal stresses that can cause osteoarthritis.

In one example, the hydrogel used is BC-PVA-PAMPS, as described above. For example, FIGS. 10B-10C show characteristic properties of various hydrogels, including BC-PVA-PAMPS and other strong hydrogels, showing that a BC-PVA-PAMPS hydrogel may have cartilage-like compressive strength/tensile strength and compressive modulus/tensile modulus properties. The hydrogels may also exhibit cartilage-equivalent tensile fatigue at 100,000 cycles. A BC-PVA-PAMPS hydrogel may be formed by infiltrating a bacterial cellulose (BC) nanofiber network with a PVA-PAMPS double network hydrogel, thereby creating a BC-PVA-PAMPS hydrogel. The BC provides tensile strength in a manner analogous to collagen in cartilage. PVA provides an elastic restoring force, viscoelastic energy dissipation, and prevents stress concentration on individual BC fibers. The PAMPS (poly(2-acrylamido-2-methyl-1-propanesulfonic acid sodium salt)) provides a fixed negative charge and osmotic restoring force similar to the role of aggrecan in cartilage. The hydrogel has the same aggregate modulus and permeability as cartilage, resulting in the same time-dependent deformation under confined compression. The hydrogel is not cytotoxic, has a coefficient of friction 45% lower than cartilage, and is 4.4 times more wear-resistant than a PVA hydrogel. The properties of this hydrogel make it an excellent candidate material for replacement of damaged cartilage.

A hydrogel may be attached to a titanium base with the porosity necessary for bone ingrowth. The implant curvature, hydrogel thickness, implant diameter, and implant position on the stress distribution for the tissue surrounding a hydrogel-capped titanium implant may be selected. The hydrogel may be attached to porous titanium with the same shear strength of the osteochondral junction (e.g., 7.25 MPa). The hydrogel may be assembled on the surface of the implant starting with a dry state (e.g., the nanofibrous portion), so that water will not interfere with adhesion to the macromolecular component of the hydrogel. In addition, the nanofibrous portion may be cemented in (dry) prior to impregnating with the rest of the hydrogel (e.g., the double network), resulting in a structure that mimics the calcified collagen anchors cartilage to bone.

Examples of hydrogel coating formed in this manner are compared to other hydrogel attachments, as shown in FIG. 9. The resulting apparatuses have achieved a shear strength of 2.28 MPa, which is a 3-fold increase over all other currently achievable hydrogel attachments. A strength exceeding 7.25 MPa may be achieved.

FIGS. 11A-11C and 12A-12B illustrate parameters of cartilage-implant constructs that may be representative of human knee morphology. Average values for cartilage thickness and radius of curvature may be used to represent median male and female specimens. Implants may have a double curvature or single curvature to match native anatomy. A tibial cartilage may be used to impart loads on the fixed femur construct, where loading will be based on peak compression values from instrumented total knee replacements. Each set of loads may be evaluated for two alignment conditions; centered on the implant and at the implant to cartilage transition. See, e.g., FIGS. 12A-12B.

Figure 7A:
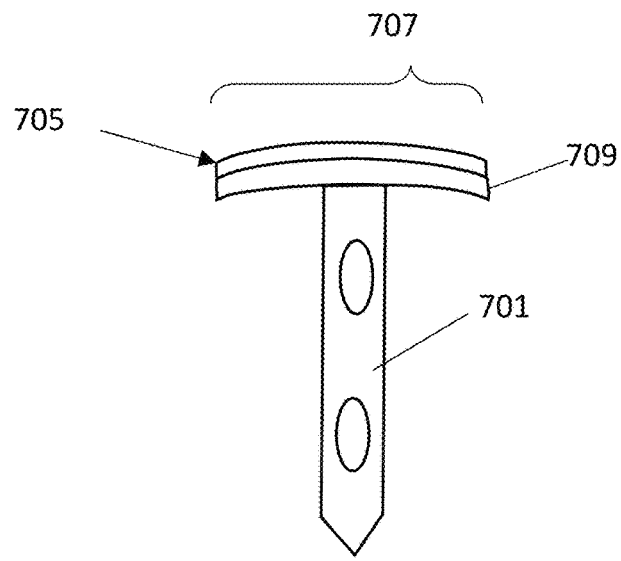
FIGS. 7A and 7B schematically illustrate examples of implants including a hydrogel attached (e.g., forming the surface) as described herein.
Figure 7B:
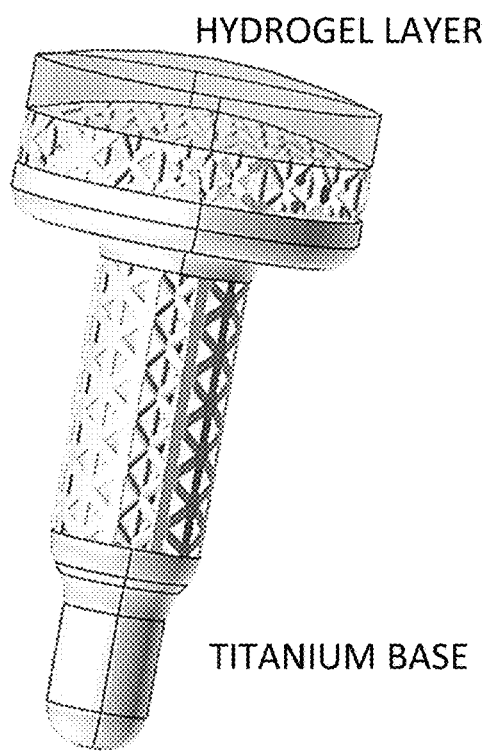

As used herein, an implant may have any appropriate structure for implanting into a body. In some (non-limiting) examples, the implants may have a shape that allows them to be implanted into bone, with a hydrogel attached to an outward-facing side. For example, FIGS. 7A and 7B illustrate examples of implants to which a hydrogel has been attached, as described herein. In FIG. 7A, the implant includes a base 701 (e.g., a titanium base) having an elongate pin-shape that may be, for example, 2 mm×7 mm (tapering to about 1.5 mm at about 3 mm from the end). The base may include one or more channels, openings, passages, etc. for ingrowth of bone. The implant also includes a top portion 705 that may be curved (e.g., with a single curvature or a double-curvature. For example, the surface may be curved with a radius of curvature of about 17 mm (single curvature) or about 19 mm×12 mm (double curvature). In FIG. 7A the top is approximately 7 mm in diameter 707. The outer surface of the implant may be approximately 1 mm thick or thicker 709 and may be about 70% porous, or greater. The hydrogel may be attached to the top surface. The hydrogel in this example is a triple-network hydrogel of BC-PVA-PAMPS and the BC is cemented to the porous top, while the PVA-PAMPS is impregnated into the BC.

Figure 12A:
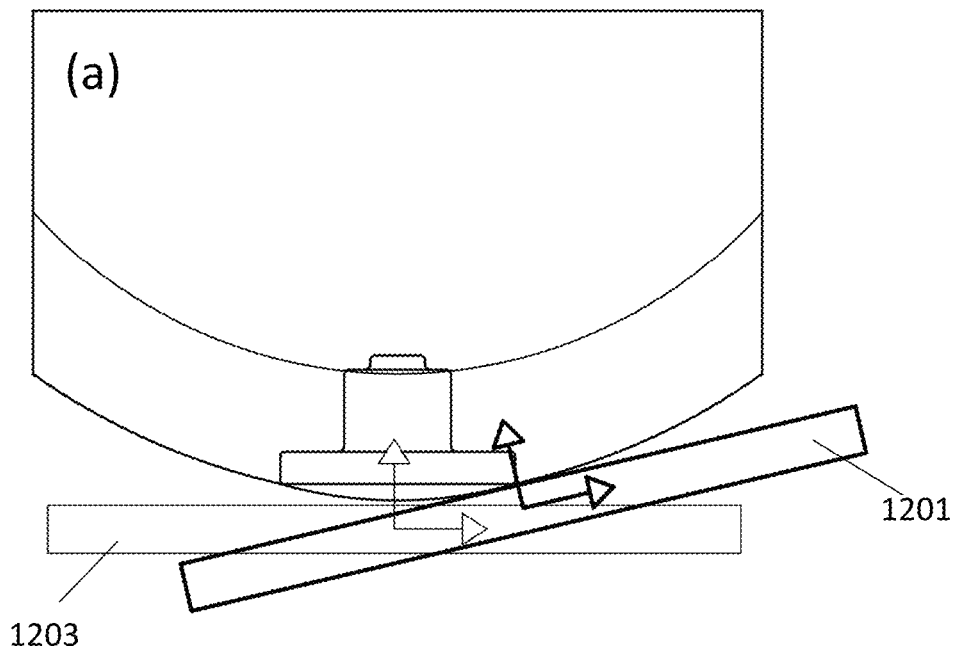
FIGS. 12A-12B show side and isometric views, respectively, of an example of an implant and bone/cartilage construct. The green rectangle represents centered loading while the blue shows loading at the edge of the implant.
Figure 12B:
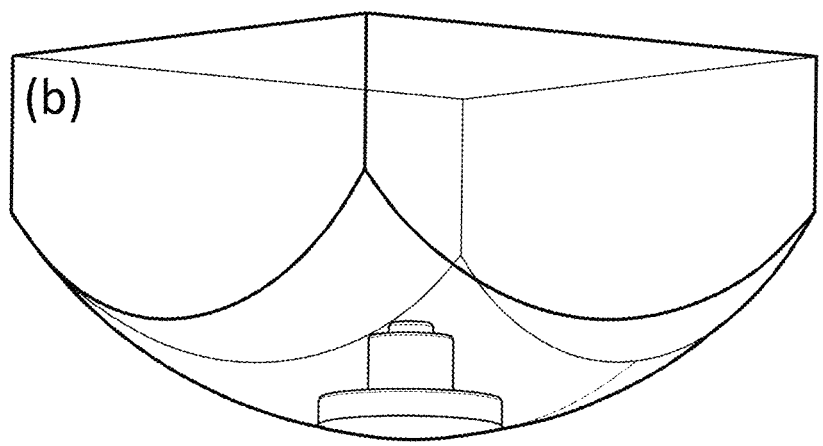

FIG. 7B shows a similar implant to that shown in FIG. 7A, in which a hydrogel is attached (e.g., via cementing the nanofibrous portion of the hydrogel to the porous surface of the implant, as shown. The implant in FIG. 7B is titanium. An implant may be designed as shown in FIGS. 11A-11C, so that the shape and/or dimensions of the implant approximately match the patient's anatomy. In FIG. 11A, the implant 1101 is shown inserted into the bone, and the hydrogel portion may have a thickness that is approximately the same as the cartilage in the bone (e.g., femur). FIG. 11B shows some of the dimensions of the implant that may be selected (e.g., implant radius, hydrogel thickness, etc.). FIGS. 12A-12B show examples of simulations of an implant as described herein implanted into a bone (e.g., femur head). In FIG. 12A two radiuses of curvature 1201, 1203 are shown. FIG. 12A shows a section through the three-dimensional simulation of FIG. 12B.

Figure 13A:
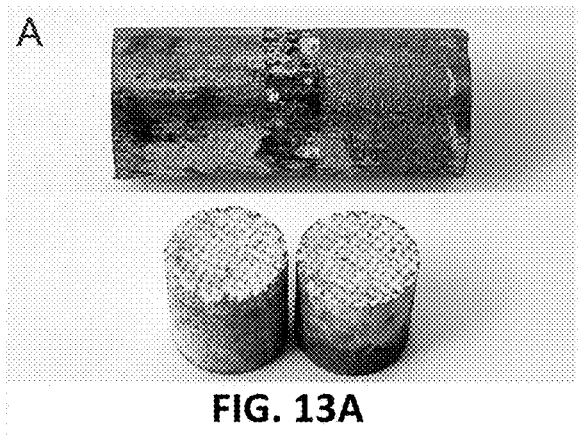
FIG. 13A shows two titanium plugs bonded with RelyX Ultimate cement before (top) and after (bottom) shear testing.

The shear strength of different cements were first tested between two titanium plugs topped with a 1-mm-thick layer of 3D printed struts with a porosity of 70%. In the case of the α-TCP cement, the sandwich structure was pressed together in a die at 250 MPa to reduce the porosity of the cement. The other plugs were pressed together by hand. An example image of a sample made with a RelyX Ultimate cement before and after shear testing is shown in FIG. 13A.

Figure 13B:
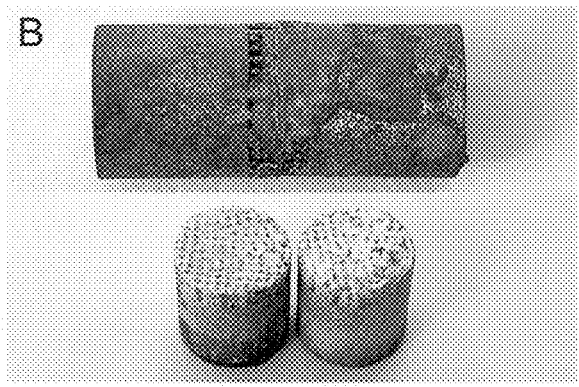
FIG. 13B shows two titanium plugs bonded to BC-PVA-PAMPS hydrogel with RelyX Ultimate cement before (top) and after (bottom) shear testing.
Figure 13C:
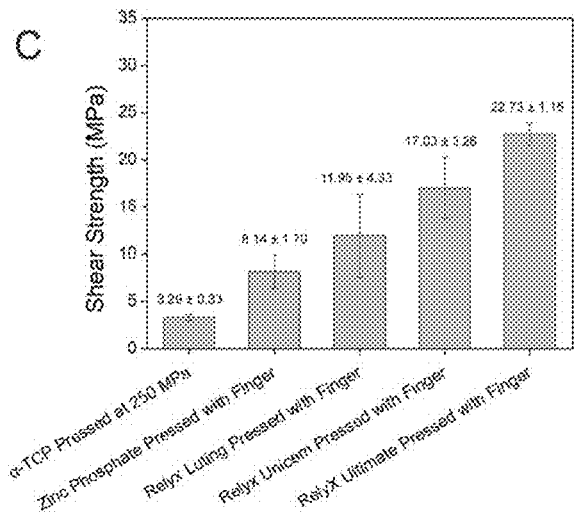
FIG. 13C is a graph illustrating the adhesive shear strengths of two titanium plugs bonded with various cements.
Figure 14:
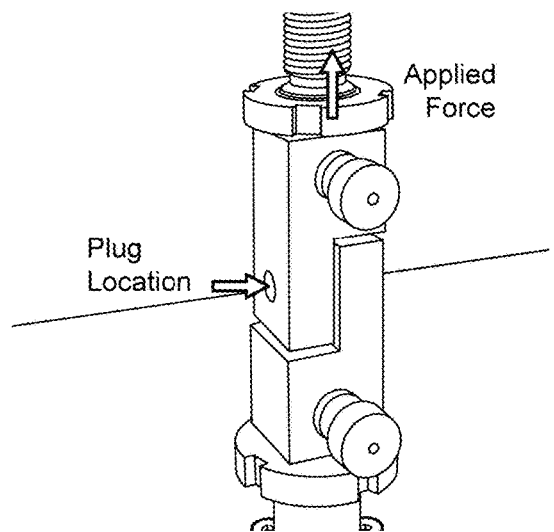
FIG. 14 shows an image of shear test fixture 1, used for shear testing of the plug-to-plug samples shown in FIGS. 13A and B.

Shear testing was performed on a Test Resources 830LE63 Axial Torsion Test Machine equipped with a 100 lb. load cell and a custom-made shear testing fixture (see FIG. 14). Note that in this "plug-to-plug" sample configuration, the shear force is applied evenly over the entire area of attachment. As shown in FIG. 13B, all the alternative cements that were tested exhibited higher shear strengths than α-TCP cement for bonding two porous titanium plugs. All sample fracture surfaces indicated cohesive failure similar to the RelyX™ Ultimate cement sample shown in FIG. 13A.

The attachment of the same cements to the BC-PVA-PAMPS hydrogel in a sandwich structure was also tested. The sample was prepared by cementing a BC sheet between the titanium plugs. The sample was either pressed together by hand for 2 minutes, or for 1 hour at 250 MPa. PVA and PAMPS were then infiltrated into the BC to create a hydrogel. An image of a sample prepared with the RelyX™ Ultimate cement is shown in FIG. 13B.

In contrast to the results for bonding porous titanium, none of the alternative cements pressed by hand increased the shear strength of hydrogel attachment relative to α-TCP pressed at 250 MPa. The relatively low strength of attachment may be due to a lack of penetration of the cements into the nanofibrous BC matrix. This hypothesis was tested by pressing the other cements at 250 MPa in the wet state prior to curing, similar to the case of α-TCP. The application of pressure increased the shear strength for each alternative cement. However, none of the shear strengths were significantly greater than that achieved with α-TCP. It was surprising that the RelyX™ Ultimate cement, for example, exhibited a shear strength 6.9 times higher than α-TCP for bonding porous titanium, but did not significantly increase the shear strength for bonding the hydrogel.

Figure 13D:
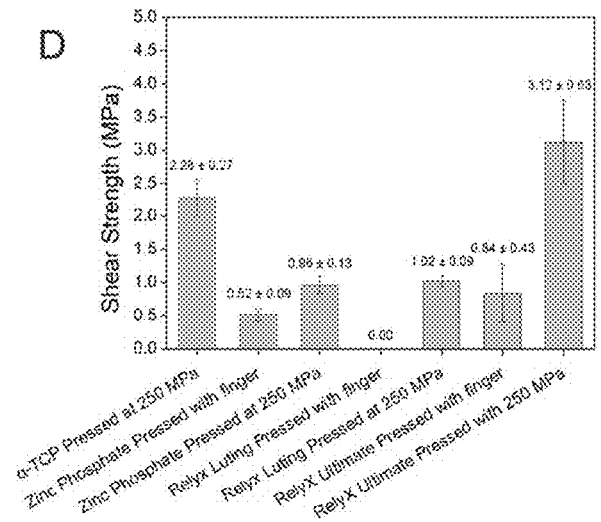
FIG. 13D is a graph of the adhesive shear strengths of two titanium plugs bonded to the BC-PVA-PAMPS hydrogel with various cements.
Figure 13E:
FIG. 13E is a SEM image of the fracture surface in FIG. 13A.
Figure 13F:
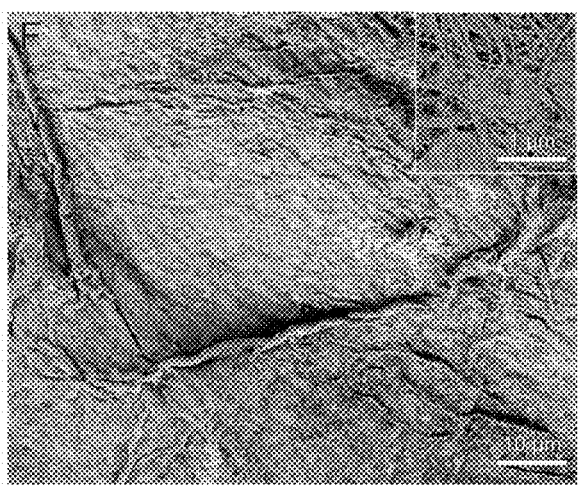
FIG. 13F is a SEM image of the fracture surface in FIG. 13B.

Scanning electron microscopy (SEM) images of the fracture surfaces for the porous titanium (FIG. 13E) and hydrogel (FIG. 13F) samples were taken to determine the reason for the lower shear strength of the hydrogel samples. For the porous titanium sample (FIG. 13E), a number of smooth fracture surface are visible in the SEM image, indicating failure was due to the fracture of the cement. However, in the case of the hydrogel sample, no smooth fracture surfaces are visible for the cement. Instead, the SEM image shows the nanofibrous surface of the BC. No fiber pull-out or fiber fracture is readily apparent in the image. Rather, it appears as though failure was due to delamination of the layers of nanofibers in the BC.

In general, the sheer strength of the connection between the hydrogel and the substrate may be dramatically enhanced by including a hydrogel including a bacterial cellulose in which the fibers of the BC have been aligned so that the fibers are perpendicular to the substrate surface.

Figure 15:
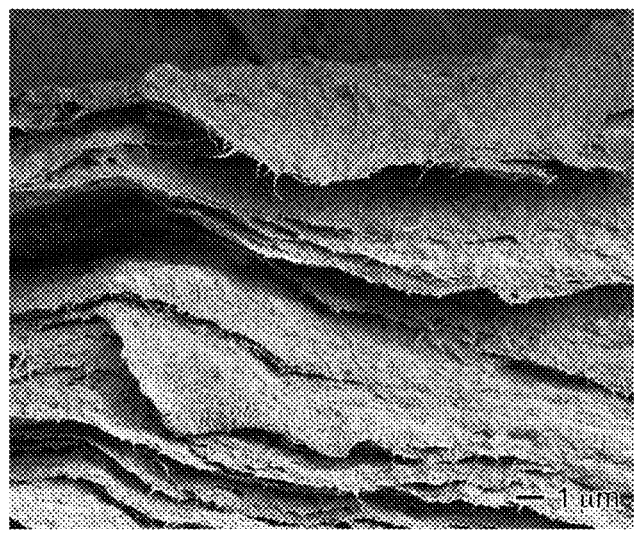
FIG. 15 is an SEM image of a cross-section of a bacterial cellulose sheet.

FIG. 15 shows the layered structure of the BC, e.g., in a sheet of commercially available BC, which is readily apparent when imaged by SEM in a direction perpendicular to the sheet. This sample was prepared by freeze-drying and cutting the BC. The layered nature of BC has been noted in a number of previous studies. It is typically due to the layer-by-layer construction of the BC film by bacteria at the air-liquid interface. Studies of collagen in cartilage have indicated it also has a layered structure, albeit one in which the layers start by being oriented perpendicular to bone and then curve over to be parallel to the cartilage surface. The structure of collagen layers in cartilage suggests the attachment strength of a hydrogel such as a BC-PVA-PAMPS hydrogel can be increased if the BC layers are curved over such that the nanofiber sheets in the BC are oriented perpendicular to the direction of shear. A perpendicular orientation of the nanofiber sheets relative to the direction of shear should increase the shear strength because removal of the hydrogel (e.g., BC-PVA-PAMPS) from the titanium may require fracture of the BC nanofibers. In contrast, shear-induced fracture of the (e.g., BC-PVA-PAMPS) hydrogel in a direction parallel to the surface of the BC sheets may involve delamination of the layers and breaking relatively few nanofibers (see, e.g. FIG. 13F). Thus, the connection between the hydrogel and the substrate may be significantly stronger in the plane of the fiber sheets than out of plane. Indeed, the highest shear strength achieved in FIG. 13D (3.12 MPa) is approximately 6 times lower than the tensile strength of the hydrogel, a test which involves nanofiber fracture.

In some examples, the methods for orienting the BC nanofibers in the hydrogel perpendicular to the direction of shear described herein may include wrapping the hydrogel around the periphery of the metal plug and securing the hydrogel in place with a clamp. The clamp may be a shape memory alloy clamp, e.g., initially in a deformed state; upon heating, the clamp may shrink to a memory shape. The clamp may apply a high clamping force. For example, a ring clamp may have a diameter of between 5 mm and 50 mm (e.g., between 10-40 mm, between 15 and 35 mm, etc.), and a ring thickness of between about 0.1 mm and 0.4 mm (e.g., about 0.27 mm), and a height of between about 0.5 mm and 4 mm (e.g., about 1 mm). In one example, the shape memory alloy clamp may, upon heating, provide a nominal clamping force of about 300 N (67 lbf). In some examples a NiTiNb shape memory alloy (Alloy H from Intrinsic Devices, Inc.) was chosen for the clamp due to its convenient operating temperature and large temperature range over which the clamping force is maintained. For this alloy, the full clamping force is obtained at 165° C. and is maintained from −65° C. to +300° C. The NiTiNb alloy is also more corrosion resistant than NiTi, which is used currently in implants, suggesting that it is biocompatible. Alternatively, a NiTi alloy may be used.

Figure 16:
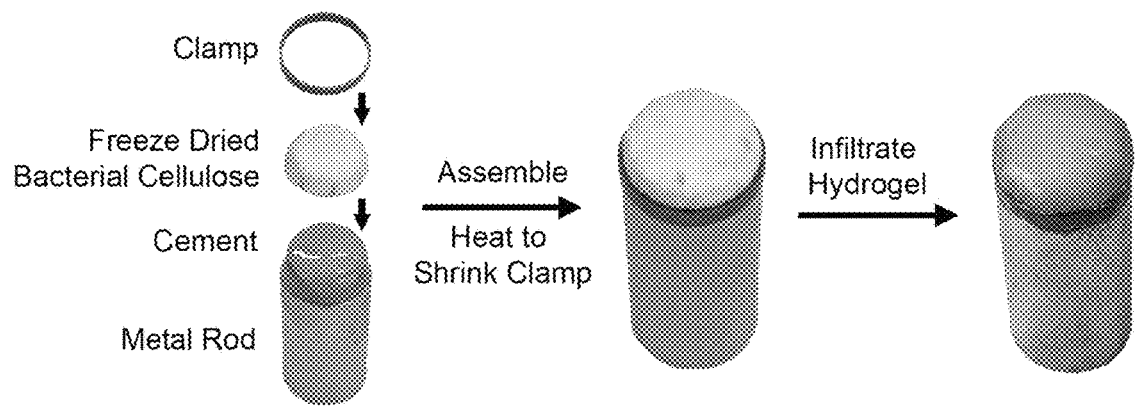
FIG. 16 is an image illustrating one example of a method of attaching a hydrogel to a metallic plug, including using a clamp (e.g., a shape memory alloy clamp) as described herein.
Figure 17:
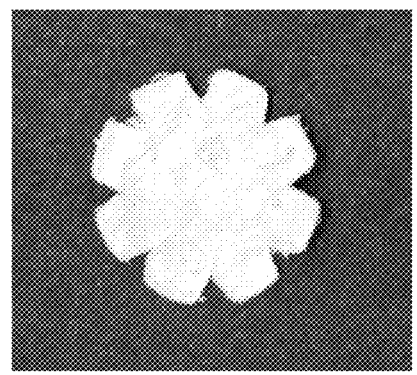
FIG. 17 is an image showing one example of a sheet of bacterial cellulose (BC) cut (e.g., with legs or crenellations) for wrapping over the edge of the metal rod as described herein.

A brief overview of how the hydrogel is attached to a metal base is illustrated in the example of FIG. 16. In this example freeze-dried BC sheets were cut into octagonal shapes with 8 projections (e.g., "legs") that can be bent over the edges of the implant, as shown in the example of FIG. 17. This cut may remove excess BC that would otherwise be folded up on the sides of the cylinder. The pieces of cut BC were then placed into a fixture, similar to that shown in FIG. 6, that facilitated centering and alignment of the ring clamp with the pieces of BC and the metal rod, which in this case was stainless steel. The metal rod was pushed down through the fixture so that the ring pushed the pieces of BC onto the metal rod. This process of pushing the ring over the BC and onto the rod could also in theory be done by hand. The use of an alignment features, such as shown in FIGS. 18A-18B may help consistently center the pieces during assembly. The sample may then be clamped, e.g., by heated in an oven at 90° C. to initiate clamping in a shape-memory alloy material preset as described herein (which starts at a temperature of 50° C.). The part was then heated in a hydrothermal bomb at 120° C. for 24 hours with PVA to infiltrate the polymer into the BC. Finally, the BC-PVA was infiltrated with PAMPS by soaking in a solution of 30% AMPS (2-acrylamido-2-methylpropanesulfonic acid) with 9 mg/mL MBAA crosslinker, 5 mg/mL 12959 and 0.5 mg/mL KPS for 24 hours. The sample was cured with UV for 15 minutes, followed by curing at 60° C. for 8 hours for heat curing.

The clamp and/or substrate may be configured to prevent breaking the bacterial cellulose. For example, the distance between the inner diameter of the ring and the outer diameter of the rod may be adjusted to achieve a high clamping force without breaking the BC. For attachment of three pieces of BC to the metal rod in one example, the outer diameter of the rod was about 5.7 mm, and the inner diameter of the ring was about 6.4 mm, leaving 0.7 mm for the three pieces of BC. Each piece of frieze-dried BC was 0.136±0.026 mm, leaving 0.3 mm of space. The ring can shrink to a diameter of 6.15 mm to consume this space and firmly clamp the BC onto the metal. In addition, the BC will expand by about 0.2 mm after infiltration of the hydrogel components. Note that the tolerances of the parts are ±0.13 mm. Reducing the space between the rod and the ring in some cases led to a greater failure rate due to breaking the legs off the BC when the ring was pushed across the BC layers. Using a larger distance between the rod and ring led to a less secure attachment of the hydrogel to the rod. Through trial and error, we found that leaving about 0.23 mm of clearance for each piece of BC was sufficient to firmly clamp the BC in place without breaking off the BC legs when sliding the ring over the BC.

The strength of attachment of the hydrogel to the rod was then compared to the strength of attachment of cartilage to bone. This was not possible with the plug-to-plug configuration used for the samples in FIGS. 13A-13B, because there is no way to attach a rod to the surface of cartilage with the same strength as the osteochondral junction. Previous tests of the shear strength of the osteochondral junction have used an L-shaped jig that pulls a square-shaped piece of cartilage off bone while constraining the movement of cartilage in a direction perpendicular to the shear plane. To perform a similar test with the cylindrical specimen described herein, a shear test fixture such as the one shown in FIG. 19 was used. The test specimen was secured in a cylindrical hole in the left side of the fixture. The right side of the fixture was machined to have a complementary half-cylinder that was used to push the hydrogel or cartilage off of their substrates. A crosshead displacement rate of 2 mm/min was used for all the measurements. While fixture 1 in FIG. 14 applies the shear force relatively evenly over a given interface, fixture 2 in FIG. 19 focuses the applied force on one edge of the rod. This difference in the manner in which the force is applied is expected to lead to a lower observed shear force in fixture 2 relative to fixture 1, especially since fixture 2 can potentially cause cleavage and peel stresses.

Figure 21A:
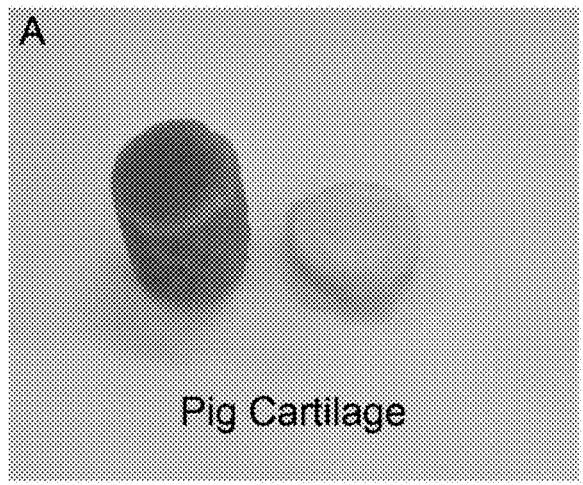
FIGS. 21A-21D show images of samples of materials tested (e.g., tested as shown in FIG. 20A).

FIGS. 20A-20B show the results for shear testing samples with shear test fixture 2. Pig cartilage had an average shear strength of about 1.16±0.35 MPa. FIG. 21A shows the cartilage was sheared cleanly off of the underlying bone in this sample. The lower shear strength of cartilage measured with fixture 2 relative to previous work (2.45±0.85 to 2.6±0.58 MPa) was likely due to the cylindrical shape of our specimens, which may concentrate stress over a smaller area at the edge of the specimen compared to the rectangular specimens tested previously. Although stress concentration was at least partially avoided by shearing the sample with a matching cylindrical surface, some concentration of shear stress may still be present. In addition, there may have been some peeling and/or cleavage in addition to shear due to imperfect alignment or imperfect constraining of the cartilage from moving out of the shear plane. Although a lower number was obtained for the shear strength of cartilage than previous authors, the direct comparison with hydrogel samples in the same fixture provided herein still provide a valid answer to the question of whether cartilage-equivalent shear strength was achieved. Further, the standard deviation of the cartilage shear strength measurements described herein are lower than those obtained previously, indicating the measurement method is at least as precise as previous efforts.

Figure 21B:
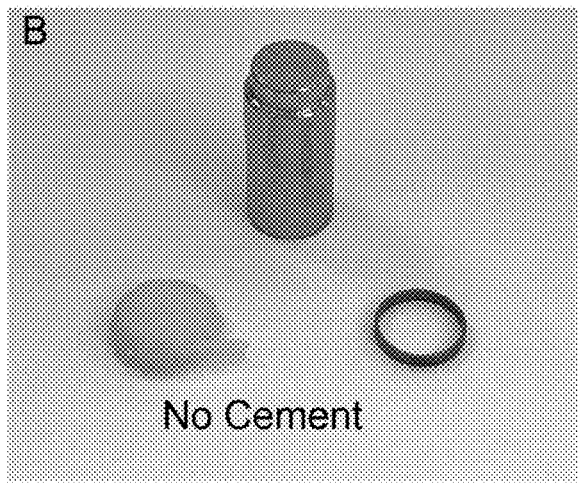

By using a clamp (e.g., a shape memory material clamp) without cement, a hydrogel sample with three layers of BC was attached to the metal rod with a shear strength of 0.98 MPa. We note that this result is within the error of the average shear strength for pig cartilage, indicating cartilage-equivalent shear strength can be achieved with the clamp alone. FIG. 21B shows the attachment failed due to the hydrogel being pulled out of the clamp. The hydrogel was also dented where it was contacted by the shear fixture (not visible in FIG. 21B).

Figure 21C:
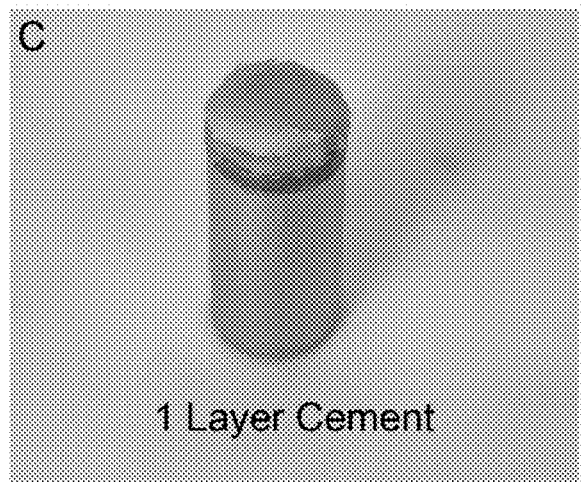

The addition of 1 layer of cement between the hydrogel and the metal rod further increased the strength of attachment, to 1.03±0.34 MPa. However, the increase in this example cannot be said to be statistically significant given the standard deviation of the measurements. This result indicates the addition of cement underneath the first layer of BC does not significantly increase the strength of attachment beyond what was achieved with the clamp alone. The addition of cement did change the failure mode to fracture of the hydrogel (as shown in FIG. 21C) rather than pull-out of the hydrogel from the clamp (as shown in FIG. 21B). The failure mode in FIG. 21C is preferable in the context of a hydrogel-capped implant because the hydrogel is still covering the metal and not exposing an opposing cartilage surface to wear by a metallic surface, for which the coefficient of friction is higher than the hydrogel.

Next, a sample with 3 layers of cement, one layer beneath each of the three BC layers, was examined. In this case the average strength increased to 1.76±0.88 MPa. This average shear strength exceeds that measured for the pig cartilage samples, but the standard deviation makes the difference in measurements not statistically significant. The addition of cement in between the layers may have increased the average strength by creating a layered composite of cement between each of the BC layers that reinforced the hydrogel. The failure mode for this sample (FIG. 21D) was similar to the case of 1 layer of cement.

Figure 21D:
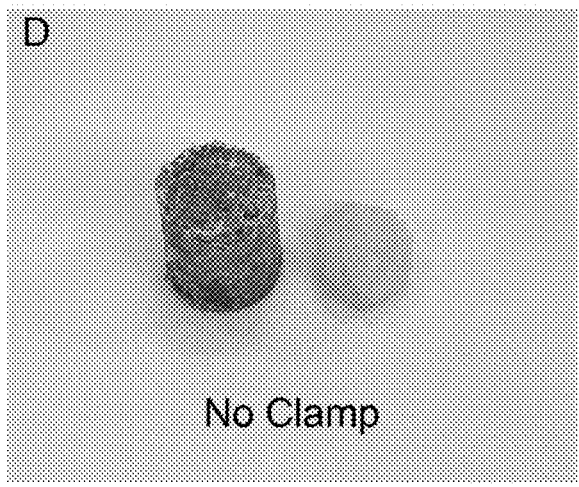

A sample in which the hydrogel was attached to the surface of the metal rod with only the cement and not the clamp was also examined. This sample proved impossible to make because, without the clamp, the hydrogel detached from the metal pin during the PVA infiltration process. Presumably the expansion of the hydrogel during PVA infiltration created a sufficient shear force to detach the hydrogel from the surface of the smooth metal rod. Instead, we attached 3 layers of hydrogel to a porous titanium plug with cement between each layer. This sample was prepared with Rely X Ultimate cement and was pressed at 250 MPa, similar to the best result in FIG. 13D. Shear testing of this "no clamp" sample with fixture 2 yielded a shear strength of 0.93±0.21 MPa. Note that this shear strength is 3.4 times lower than the shear strength of 3.12±0.63 measured with fixture 1, indicating that method of measurement used with fixture 2 leads to a lower observed shear strength for a sample with an identical interface. FIG. 21D shows this sample failed cohesively in a similar manner as the cartilage sample. We note that while this shear test result without the clamp was lower than the samples tested with the clamp and cement, the difference was not statistically significant.

The way in which the samples made with the shape memory alloy clamp fractured (see for example FIG. 21C) suggests that the shear strength of the samples is limited by the tensile force required to fracture the hydrogel that is curved over the edge of the implant. The shear test pushes the hydrogel off of the metal pin, which creates a tensile force on the hydrogel that is clamped around the sides of the pin. This tensile force can either pull the hydrogel out of the clamp (as shown in FIG. 21B) or cause the hydrogel around the periphery of the pin to fracture (as shown in FIG. 21C). These results suggest that the shear strength of attachment can be increased by making the hydrogel layer thicker. FIG. 20B shows the results testing this hypothesis. As expected, the shear strength of attachment increases as the number of BC layers is increased from two to five. Each of these samples had one layer of cement in between the BC layer and the metal pin, and all failed cohesively (see, e.g., FIGS. 22A-22C). The p-value from one-way ANOVA for the 2 layer vs. 5 layer result is 0.039, indicating the difference in these results is statistically significant (p<0.05). The shear strength of the five-layer BC hydrogel was one standard deviation above the average shear strength of the pig cartilage.

In any of the methods and apparatuses described herein, the nanofiber network (e.g., Bacterial Cellulose, BC) may be clamped onto the implant. The nanofiber network may also be cemented. In some examples the nanofiber network may be clamped but not cemented. In some examples, the nanofiber network is both clamped (which may align the fibers, as described herein) and cemented.

Described herein are hydrogel-capped implants. In some examples the hydrogel-capped implants may include a BC containing hydrogel that is clamped to a portion of the implant that is perpendicular to the tissue-engaging surface of the implant. Alternatively or additionally, the BC containing hydrogel may be bonded via an adhesive) to a portion of the implant that is perpendicular to the tissue-engaging surface; the adhesive may be cured under pressure (e.g., under between about 150 MPa and 500 MPa, e.g., about 250 MPa). Any of these apparatuses may include multiple layers of BC that may (optionally) be adhesively secured together.

For example, any of these apparatuses may include a clamp that is used to secure a sheet of BC to the implant; the hydrogel may be formed in the BC so that the BC is part of a network (e.g., triple network hydrogel). Thus, the final apparatus may include a clamp as described herein. In some examples, these clamps may be shape-memory alloy clamps, formed as rings or loops that can be produced in a variety of shapes and sizes for clamping hydrogels to the surface of implants for repair of osteochondral defects. FIG. 23 shows an example of a clamp to attach the hydrogel (e.g., BC-PVA-PAMPS hydrogel) to an osteochondral implant with a diameter of 20.64 mm. In this example five pieces of BC were cut into shapes with 8 octagonal legs that allowed the legs to fold over the edge of the implant. A 0.25-mm-thick coating of commercially pure titanium was applied to the stem of the implant and underneath the base with a plasma spray process in order to improve integration with bone. The top surface of the implant is curved to match the native curvature of the knee. Once the one or more layers of BC are applied and clamped onto the implant, as shown in the middle of FIG. 23, the BC may be infiltrated with the remaining hydrogel components (e.g., PAMPS, PVA) to form the final hydrogel, as described herein.

Any appropriate shape or dimensions of the implant may be used. For example, if a patient is suffering from an elongated or oblong cartilage defect that cannot be adequately treated with a circular device, a rectangular, oval, or cartouche-shaped device can be used to treat the defect. FIG. 24 shows an example of a cartouche-shaped clamp that can be used to press an appropriately cut piece of BC onto a cartouche-shaped implant.

In the examples shown and described herein the Bacterial Cellulose (BC) was formed as a sheet. For example, a sheet of BC (Gia Nguyen Co. Ltd.) may be combined and manipulated dry and attached to the substrate as described herein. In some examples (e.g., forming BC-PVA-PAMPS hydrogels), Poly(vinyl alcohol) (PVA) (fully hydrolyzed, molecular weight: 145,000 g mol-1), N,N'-methylenediacrylamide (MBAA, 97.0%), 2-hydroxy-4'-(2-hydroxyethoxy)-2-methylpropiophenone (12959), potassium persulfate (KPS), 2-acrylamido-2-methylpropanesulfonic acid sodium salt (AMPS, 50 wt. % solution in water) and phosphoserine (e.g., Sigma Aldrich) may be used. Phosphate buffered saline (PBS) may be used for rinsing and hydrating. Examples of adhesives that may be used include, e.g., Ti-18Al-4V ELI (Grade 23) powder (3D Systems), α-tricalcium phosphate (α-TCP) (Goodfellow Corporation), Zinc phosphate cement (Prime-Dent), RelyX Luting 2 (3M ESPE), RelyX Unicem (3M ESPE), RelyX Ultimate cement (3M ESPE) and Scotchbond Adhesive (3M ESPE).

In general, the implant forming the substate may be any appropriate, biocompatible material, include metals and polymers. For example, in some cases titanium may be used. Titanium plugs in FIGS. 16 and 21A-22C were fabricated via selective laser melting (SLM) of Ti-18Al-4V ELI powder on a titanium substrate in an inert argon atmosphere using a 3D Systems DMP ProX 320. Plugs (test samples) were designed to have a diameter of 6 mm and a height of 6.35 mm. The final implants described herein may be any appropriate shape and size. In these examples, the top 1 mm of the plug was composed of a porous strut structure with a porosity of 70%, which may help with adhesive bonding, when adhesives are used (optionally). After printing, the samples were removed from the build plate via wire electrical discharge machining and cleaned by sonication for 15 min in DI water to remove the excess unadhered powder.

As described above, several cements were tested between two porous titanium plugs. To prepare the sample with α-TCP cement, a dry cement mixture consisting of 0.040 g phosphoserine (PPS), 0.312 g of α-TCP and 0.048 g of stainless-steel powder (SSP) was placed into a small dish, 0.140 ml of water was added, and the powder was rapidly mixed with the water. Approximately 0.150 ml of the wet cement mixture was added on top of a porous titanium plug in a metal die with an inner diameter of 6 mm. A second titanium plug was immediately placed into the die with the porous layer in contact with the wet cement, and the sandwich structure was pressed together for 1 hour at 250

MPa. The sample was placed into water at 85° C. for at least 24 hours to facilitate the transformation of α-TCP into hydroxyapatite and was stored in water until just prior to shear testing.

To prepare the sample with zinc phosphate cement, approximately 1 g of the liquid were mixed with 2 g of powder for 90 seconds. The addition of the powder into the liquid was carried out slowly, smoothly and carefully with constant stirring. After that, approximately 0.150 ml of the wet zinc phosphate cement mixture was added on top of the first porous titanium plug in a metal die with an inner diameter of 6 mm. The second titanium plug was immediately placed into the die with the porous layer in contact with the wet cement, and the sandwich structure was pressed together for 1 hour at 250 MPa with a hydraulic press or for 2 minutes by hand. After the cement was completely dry (~2 hours), the sample was placed into water at 22° C. for at least 24 hours and was stored in water until just prior to shear testing.

To prepare the sample with RelyX™ Luting 2 and RelyX™ Unicem cement, approximately 0.150 ml of the wet RelyX™ Luting 2 or RelyX™ Unicem cement mixture was added on top of the first porous titanium plug in a metal die with an inner diameter of 6 mm. The second titanium plug was immediately placed into the die with the porous layer in contact with the wet cement, and the sandwich structure was pressed together for 1 hour at 250 MPa with a hydraulic press or for 2 minutes by hand. The sample was placed into water at 22° C. for at least 24 hours was stored in water until just prior to shear testing.

To prepare the sample with RelyX™ Ultimate cement, Scotchbond Adhesive was first applied to the porous surfaces of both titanium plugs. The adhesive was allowed to set for 20s before being blown by air for another 5 s. After that, approximately 0.150 ml of the wet RelyX™ Ultimate cement mixture was added on top of the first porous titanium plug in a metal die with an inner diameter of 6 mm. The second titanium plug was immediately placed into the die with the porous layer in contact with the wet cement, and the sandwich structure was pressed together for 1 hour at 250 MPa with a hydraulic press or for 2 minutes by hand. The sample was placed into water at 22° C. for at least 24 hours and was stored in water until just prior to shear testing.

As mentioned, all of the hydrogel samples described herein were made with freeze-dried BC. BC sheets were cut and placed between 2 metal plates. A 6.59 kg weight was applied to the metal plate to flatten the BC sheets. The BC sheets were frozen at −80° C. and then in liquid nitrogen. Note that if the BC sheets are placed directly into liquid nitrogen without the pre-freezing step they fractured. The BC sheets were then removed and freeze-dried at −78° C. for 24h.

Samples for Hydrogel Plug-to-Plug Shear Testing were made using each of several cements to attach the hydrogel between two porous titanium plugs to test the adhesive shear strength. For the α-TCP sample, a cement mixture consisting of 0.080g PPS, 0.624 g of α-TCP, and 0.096 g of SSP was placed into a small dish, 0.280 ml of water was added, and the powder was rapidly mixed with the water. Then 0.150 ml of the wet cement mixture was added on top of the porous titanium plug in the die. The Freeze-Dried BC sheet was then placed on top of the cement in the die, and an additional 0.150 ml of the wet cement mixture was added on top of the BC sheet. A second porous titanium plug was then placed on top of the Freeze-Dried BC sheet in the die to create a sandwich structure. The sandwich structure was pressed for 1 hour at 250 MPa. The sample was placed into water at 85° C. for 24 hours to facilitate the transformation of α-TCP into hydroxyapatite. The sample was then placed into a hydrothermal reactor with a mixture of PVA (40 wt. %) and DI water (60 wt. %) to infiltrate PVA into the BC layer. The sample was frozen at −78° C. and thawed to room temperature to further increase the strength of the hydrogel. The sample was then soaked in a solution containing AMPS, (30 wt. %) cross-linker (MBAA, 60 mM), and heat initiator (potassium persulfate, 0.5 mg ml$^{-1}$) for 24 hours. The hydrogel was heat cured at 60° C. for 8 hours and the sample was soaked in DI water for at least 24 hours.

For the zinc phosphate cement, approximately 1 g of the liquid were being mixed with 2 g of powder for 90 seconds. The addition of the powder into the liquid was carried out slowly, smoothly and carefully with constant stirring. Approximately 0.150 mL of the wet zinc phosphate cement mixture was added on top of the first porous titanium plug in a metal die with an inner diameter of 6 mm. The BC sheet was then placed on top of the cement in the die, and an additional 0.150 mL of the wet cement mixture was added on top of the BC sheet. The second porous titanium plug was then placed on top of the BC sheet in the die to create a sandwich structure. The sandwich structure was pressed for 1 hour at 250 MPa or for 2 minutes by hand. After the cement was completely dry (~2 hours), the sample was placed into water at 22° C. for 24 hours to rehydrate the BC. The sample was then placed into a hydrothermal reactor with a mixture of PVA (40 wt. %) and DI water (60 wt. %) to infiltrate PVA into the BC layer. The sample was frozen at −78° C. and thawed to room temperature to further increase the strength of the hydrogel. The sample was then soaked in a solution containing AMPS, (30 wt. %) cross-linker (MBAA, 60 mM), and heat initiator (potassium persulfate, 0.5 mg ml$^{-1}$) for 24 hours. The hydrogel was heat cured at 60° C. for 8 hours and the sample was soaked in DI water for at least 24 hours.

For the RelyX™ Luting 2 and RelyX™ Unicem cement, approximately 0.150 mL of the wet RelyX™ Luting 2 or RelyX™ Unicem cement mixture was added on top of the first porous titanium plug in a metal die with an inner diameter of 6 mm. The BC sheet was then placed on top of the cement in the die, and an additional 0.150 mL of the wet cement mixture was added on top of the BC sheet. The second porous titanium plug was then placed on top of BC sheet in the die to create a sandwich structure. The sandwich structure was pressed for 1 hour at 250 MPa or for 2 minutes by hand. The sample was placed into water at 22° C. for 24 hours to rehydrate the BC. The sample was then placed into a hydrothermal reactor with a mixture of PVA (40 wt. %) and DI water (60 wt. %) to infiltrate PVA into the BC layer. The sample was frozen at −78° C. and thawed to room temperature to further increase the strength of the hydrogel. The sample was then soaked in a solution containing AMPS, (30 wt. %) cross-linker (MBAA, 60 mM), and heat initiator (potassium persulfate, 0.5 mg ml$^{-1}$) for 24 hours. The hydrogel was heat cured at 60° C. for 8 hours and the sample was soaked in DI water for at least 24 hours.

For the Relyx™ Ultimate cement, Scotchbond Adhesive was first applied to the porous surfaces of both titanium plugs and both surfaces of a BC sheet. The adhesive was allowed to set for 20 seconds before being blown by air for another 5 seconds. After that, approximately 0.150 mL of the wet RelyX™ Ultimate cement mixture was added on top of the first porous titanium plug in a metal die with an inner diameter of 6 mm. The BC sheet was then placed on top of the cement in the die, and an additional 0.150 mL of the wet cement mixture was added on top of the BC sheet. The second porous titanium plug was then placed on top of the BC sheet in the die to create a sandwich structure. The sandwich structure was pressed for 1 hour at 250 MPa or for 2 minutes by hand. The sample was placed into water at 22° C. the rehydrate the BC. The sample was then placed into a hydrothermal reactor with a mixture of PVA (40 wt. %) and DI water (60 wt. %) to infiltrate PVA into the BC layer. The sample was frozen at −78° C. and thawed to room temperature to further increase the strength of the hydrogel. The sample was then soaked in a solution containing AMPS, (30 wt. %) cross-linker (MBAA, 60 mM), and heat initiator (potassium persulfate, 0.5 mg ml$^{-1}$) for 24 hours. The hydrogel was heat cured at 60° C. for 8 hours and the sample was soaked in DI water for at least 24 hours.

For preparing the pig cartilage samples used for the shear test, the pig knee was first clamped on a bench vise. An osteochondral autograft transfer system (OATS) tool was used harvest the osteochondral plug from the pig knee. The OATS donor harvester was positioned on the pig knee surface and tamped approximately 15 mm into the surface. The handle was rotated to harvest the plug and withdrawn. The pig plug was extruded out by the core extruder. The pig plug was cut to make the bone region 8 mm bone in length.

Preparation of all hydrogel samples started with cutting the freeze-dried BC. The freeze-dried BC was placed on a cutting mat that had been made to be sticky with PVA glue. The BC was cut in the shape of an octagon with an inner diameter of D mm and 8 legs which has leg lengths of L mm and widths of W=0.383D. The sample was labeled as BC-D-L after cutting. The 8-piece star shape (BC-D-L) was generated by MATLAB and loaded into Silhouette Studio software. For example, the 3 layers BC shear test sample was fabricated with BC-6-2, BC-6-1.75, and BC-6-1.75 from top to bottom. The following cutting settings were used in Silhouette Studio: Force=3, Speed=1, and Passes=3. After cutting, the BC was removed and placed in petri dish.

For adhering three pieces BC to the shear test rod with one layer of cement and a clamp, a stainless-steel test rod was machined to have a top section with a diameter of 5.7 mm and a height of 2 mm, and a bottom section with a diameter of 17 mm and a height of 13 mm. The three pieces of cut BC were placed in an alignment fixture. Scotchbond Universal Adhesive was applied to the layer of the BC in contact with the rod and the top surface of the rod. The adhesive was allowed to set for 20 seconds before being blown by air for another 5 seconds. About 0.15 g RelyX Ultimate Cement was then applied to same surfaces coated with the Scotchbond Universal Adhesive. The rod was pressed into the BC layers and then into the ring clamp. The cement was cured for 1 h. The samples were heated in an oven at 90° C. for 10 min to shrink the clamp. The sample was then soaked in DI water for 1 hr. in a centrifuge tube.

For creating the sample without the cement, the same procedure was followed as above but no adhesive or cement was applied to the BC or the rod. For creating samples with three layers of cement, additional adhesive and cement was applied as described above to between each layer of BC, in addition to between the BC and the rod. For testing samples with 2 layers of BC, the top diameter of the rod was 5.8 mm instead of 5.7 mm, and the size of the cut BC layers were BC-6-1.75 and BC-6-1.75. For testing samples with 5 layers of BC, the top diameter of the rod was 5.2 mm, and the size of the cut BC layers were BC-3-2, BC-3-2, BC-5.5-2.25, BC-5.5-2, and BC-5.5-1.75.

After attachment of BC to the metal rod, all hydrogel samples were made by infiltrating PVA and PAMPS into the BC. For infiltration of PVA, the rehydrated sample was placed in a hydrothermal bomb with 40% PVA and 60% DI water. The hydrothermal bomb was heated at 120° C. for 24 h to infiltrate PVA into the BC layers. After 24 h, the hydrothermal bomb was removed from the oven and opened while it was hot. The sample was taken out from the bomb and the extra PVA around the sample was manually removed. The sample was placed into a −80° C. freezer and taken out from the freezer after 30 minutes. The sample was thawed to room temperature before the next step, infiltration of PAMPS. The thawed sample was put into a 30% AMPS (2-acrylamido-2-methylpropanesulfonic acid) solution with 9 mg/mL MBAA crosslinker, 5 mg/mL 12959 and 0.5 mg/mL KPS for 24 h (all fully dissolved). The sample was taken out and cured with UV for 15 minutes. It was transferred to an air-tight centrifuge tube and placed into a 60° C. oven for 8 h for heat curing. After curing, the implant was placed in PBS for rehydration.

Shear testing, such as that shown in FIGS. 20A-20B, was performed on a 830LE63 Axial Torsion Test Machine equipped with a 100 lb. load cell. Each test was performed in customized shear test fixtures. For shearing of cartilage or hydrogel on metal samples, the sample was secured in a cylindrical hole in the left side of the fixture. The hole size was 6 mm for the pig plug and 7 mm for the hydrogel samples. Spacers were added underneath the samples to precisely align the shear plane to the cartilage-bone or hydrogel-metal interface. The right side of the fixture was machined to have a complementary half-cylinder that was used to push the hydrogel or cartilage off of their substrates. The diameter of the right half-cylinder matched that of the left side (either 6 or 7 mm). Rubber was placed between the sample and the right shear fixed to apply some pressure during the shear test in order to minimize cleavage and peeling. A crosshead displacement rate of 2 mm min-1 was used for all the measurements.

The methods and apparatuses described herein include a method of forming an implant including a hydrogel on an engagement surface of the implant. The engagement surface may be configured to engage a hard tissue (e.g., bone) or another implant, once inserted into a body. Although examples of implants include a bone implant 1100 such as the one shown in FIG. 23, any implant configuration may be used. In general, the implant includes an engagement surface. The engagement surface may be convex, concave, flat, or otherwise curved or shaped. The engagement surface typically includes a lip or rim region that extends approximately perpendicularly (e.g., between 70 degrees and 140 degrees, e.g., between 70 degrees and 110 degrees, approximately 90 degrees, etc.) relative to the engagement surface. The in the example shown in FIG. 23, the engagement surface is shown with a cement applied on the surface 1104, and an edge (also referred to as a rim or lip region) 1106 surrounds the engagement surface. As discussed above, one or more sheets of BC 1108 may be cut to fit over the engagement surface and down (or in the case of recessed engagement surfaces, up) the side of the approximately perpendicular edge region. In FIG. 23, the clamp 1110 may fit over the BC and edge and be activated to clamp down onto the one or more layers of BC to secure them against the edge, as shown.

FIG. 25 schematically illustrates one example of a method of securing a hydrogel (e.g., a BC containing hydrogel) onto an implant, as described herein. This method may provide a process that enables the attachment of a hydrogel to the surface of an implant (e.g., an orthopedic implant) with approximately the same or greater shear strength as the natural cartilage-bone interface. In some examples, clamping the hydrogel around the periphery of the engagement surface of the implant reorients the nanofibers in the BC so that they are perpendicular to the direction of shear. This reorientation increases the average strength of attachment by necessitating fracture of the nanofiber sheets to shear the hydrogel off the implant. Without this reorientation, the BC layers may delaminate, resulting in a lower shear strength. The methods described herein, may include clamping in conjunction with adhesive cements to further improve the strength of attachment and prevent the hydrogel from being pulled out of the clamp. The shear strength also increased with the number of BC layers used in the hydrogel, indicating the shear strength is limited by the tensile force required to fracture the hydrogel at the periphery of the implant.

For example, in FIG. 25, the one or more sheets of BC (e.g., freeze-dried BC) may be prepared before attaching to the implant. In some examples, the one or more sheets of BC may be cut so that it/they may fit over the engagement surface and may fold over the edge (e.g., lip or rim region) so that pressure may be applied uniformly against the portion of the sheet that is extending over (or in some cases around) the edge region 1301.

The edge region (lip or rim) may be any appropriate size, such as between 0.1 mm and 4 mm (e.g., between 0.2 mm and 3 mm, between 0.4 mm and 3 mm, etc.). The potion of the sheet of BC that extend over the edge region (e.g., lip or rim) may be cut, notched or otherwise formed to prevent substantial folding which may result in uneven pressure and securing force, e.g., by a clamp.

In any of these examples an adhesive, such as one or more of the adhesives described herein, may be applied to the implant before applying the sheet(s) of BC. For example, adhesive may be applied to the engagement surface and/or to the edge or rim region.

The one or more sheets may then be secured over the engagement surface and against the surrounding side(s) (e.g., the lip or rim region) by a clamp and/or by an adhesive 1303. If an adhesive is used it may be cured under pressure for an appropriate time period (e.g., under between about 100-500 MPa for greater than 4 hours, etc.). In some examples the clamp may be a ring or annulus (e.g., collet) of a shape memory alloy material that is configured to transition from a wider configuration to a shape-set narrower configuration once applied over the edge region. In variations in which the engagement surface is recessed and the edge region is raised above the engagement surface, the clamp may be expanded from a narrow to a larger, expanded diameter. The clamp may be configured to apply an amount of force sufficient to retain the sheet(s) in position, but not so large that they cut or damage the BC material.

Thereafter, the hydrogel, including the BC material of the one or more sheets of BC may be infiltrated with the remaining hydrogel component(s) to form the complete hydrogel 1305, such as a triple-network hydrogel, including the BC.

The methods of hydrogel attachment described herein can be used to create hydrogel-coated orthopedic implants with surfaces that mimic the mechanical and tribological properties of cartilage, and bases that enable integration with bone for long-term fixation.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An implant having a hydrogel bonded to a first surface of the implant, the implant comprising:
    an implant body including the first surface, wherein the first surface is porous;
    a cross-linked cellulose nanofiber network, wherein the cross-linked cellulose nanofiber network is bonded to the first surface by a cement; and
    a hydrogel impregnated in the cross-linked cellulose nanofiber network, the hydrogel extending from the first surface, wherein the hydrogel impregnated into the cross-linked cellulose nanofiber network is secured to the first surface with a shear strength that is greater than 1 MPa, wherein the cement is not bonded to the hydrogel.

2. The implant of claim 1, wherein the hydrogel is a double-network hydrogel.

3. The implant of claim 1, wherein the hydrogel impregnated into the cross-linked cellulose nanofiber network forms a triple-network hydrogel.

4. The implant of claim 1, wherein the first surface is greater than 40% porous to a depth of 1 mm or greater.

5. The implant of claim 1, wherein the cement comprises an α-TCP cement.

6. The implant of claim 1, wherein the cement comprises one or more of:
    zinc oxide eugenol, glass ionomer, calcium silicate, polycarboxylate cement, zinc phosphate, acrylate or methacrylate resin cements, and resin-modified glass ionomer cement.

7. The implant of claim 1, wherein the cement extends at least 5 microns into the cross-linked cellulose nanofiber network from the first surface.

8. The implant of claim 1, wherein the cement comprises phosphoserine (PPS).

9. The implant of claim 1, wherein the cement comprises stainless steel powder (SSP).

10. The implant of claim 1, wherein at least a portion of the cross-linked cellulose nanofiber network is mineralized.

11. The implant of claim 1, wherein the hydrogel impregnated into the cross-linked cellulose nanofiber network comprises a double network hydrogel comprises polyvinyl alcohol (PVA), and poly(2-acrylamido-2-methyl-1-propanesulfonic acid sodium salt (PAMPS).

12. The implant of claim 1, wherein the hydrogel impregnated into the nanofiber network comprises a double network hydrogel comprising poly-(N,N'-dimethyl acrylamide) (PDMAAm), copolymers of 1-vinylimidazole and methacrylic acid, amphiphilic triblock copolymers, polyampholyte hydrogels, a PVA-tannic acid hydrogel, a poly(N-acryloyl) glycinamide hydrogel, polyacrylic acid-acrylamide-C18 hydrogel, guanine-boric acid reinforced PDMAAm, polyelectrolyte hydrogels, a poly(acrylonitrile-co-1-vinylimidazole) hydrogel (a mineralized poly(acrylonitrile-co-1-vinylimidazole) hydrogel), a polyacrylic acid-Fe3+-chitosan hydrogel, a poly(methacrylic acid) gel, a graphene oxide/xonotlite reinforced polyacrylamide (PAAm) gel, a poly(stearyl methacrylate)-polyacrylic acid gel, an annealed PVA-polyacrylic acid hydrogel, supramolecular hydrogels from multiurea linkage segmented copolymers, polyacrylonitrile-PAAm hydrogel, a microsilica reinforced dimethacrylate (DMA) gel, an agar polyhydroxyethylmethacrylate gel, a poly n acryloyl ethyl trimethylammonium chloride hydrogel, a poly(3-(methylacryloylamino) propyl-trimethylammonium chloride hydrogel, a poly (sodium p-styrenbesulfonate) hydrogel, a polyethylene glycol diacrylate hydrogel, ora polyethylene glycol hydrogel.

13. The implant of claim 1, wherein the first surface of the implant body comprises titanium.

14. The implant of claim 1, wherein the first surface of the implant body comprises one or more of: a stainless steel alloy, a titanium alloy, a Co—Cr alloy, tantalum, gold, niobium, bone, Al oxide, Zr oxide, hydroxyapatite, tricalcium phosphate, calcium sodium phosphosilicate, poly(methyl methacrylate), polyether ether ketone, polyethylene, polyamide, polyurethane, or polytetrafluoroethylene.

15. The implant of claim 1, wherein an outer surface of the hydrogel has a surface roughness of less than 30 microns.

16. An implant having a hydrogel bonded to a first surface of the implant, the implant comprising:
an implant body including the first surface, wherein the first surface is porous;
a cross-linked cellulose nanofiber network, wherein the cross-linked cellulose nanofiber network is bonded to the first surface by a cement; and
a hydrogel comprising polyvinyl alcohol (PVA) impregnated in the cross-linked cellulose nanofiber network, the hydrogel extending from the first surface, wherein the cement extends at least 5 microns into the cross-linked cellulose nanofiber network from the first surface, further wherein the hydrogel impregnated into the cross-linked cellulose nanofiber network is secured to the first surface with a shear strength that is greater than 1 MPa, wherein the cement is not bonded to the hydrogel.

17. The implant of claim 16, wherein the hydrogel is a double-network hydrogel.

18. The implant of claim 16, wherein the hydrogel impregnated into the cross-linked cellulose nanofiber network forms a triple-network hydrogel.

19. The implant of claim 16, wherein the cement comprises an α-TCP cement.

20. The implant of claim 16, wherein the cement comprises one or more of:
zinc oxide eugenol, glass ionomer, calcium silicate, polycarboxylate cement, zinc phosphate, acrylate or methacrylate resin cements, and resin-modified glass ionomer cement.

21. The implant of claim 16, wherein the cement comprises phosphoserine (PPS).

22. The implant of claim 16, wherein the cement comprises stainless steel powder (SSP).

23. The implant of claim 16, wherein at least a portion of the cross-linked cellulose nanofiber network is mineralized.

24. The implant of claim 16, wherein the hydrogel impregnated into the cross-linked cellulose nanofiber network comprises a double network hydrogel comprises polyvinyl alcohol (PVA), and poly(2-acrylamido-2-methyl-1-propanesulfonic acid sodium salt (PAMPS).

25. The implant of claim 16, wherein the first surface of the implant body comprises titanium.

26. The implant of claim 16, wherein the first surface of the implant body comprises one or more of: a stainless steel alloy, a titanium alloy, a Co—Cr alloy, tantalum, gold, niobium, bone, Al oxide, Zr oxide, hydroxyapatite, tricalcium phosphate, calcium sodium phosphosilicate, poly(methyl methacrylate), polyether ether ketone, polyethylene, polyamide, polyurethane, or polytetrafluoroethylene.

27. The implant of claim 16, wherein an outer surface of the hydrogel impregnated into the cross-linked cellulose nanofiber network has a surface roughness of less than 30 microns.

28. An implant having a hydrogel bonded to a first surface of the implant, the implant comprising:
an implant body including the first surface, wherein the first surface is a porous titanium;
a cross-linked cellulose nanofiber network, wherein the cross-linked cellulose nanofiber network is bonded to the first surface by a cement; and
a hydrogel comprising polyvinyl alcohol (PVA) impregnated in the cross-linked cellulose nanofiber network, the hydrogel extending from the first surface, wherein the cement extends at least 5 microns into the cross-linked cellulose nanofiber network from the first surface but said cement is not bonded to the hydrogel, further wherein the hydrogel impregnated into the cross-linked cellulose nanofiber network is secured to the first surface with a shear strength that is greater than 1 MPa.

* * * * *